US005702866A

United States Patent [19]

Fryberg et al.

[11] Patent Number: 5,702,866
[45] Date of Patent: *Dec. 30, 1997

[54] DIHYDRAZIDES

[75] Inventors: Mario Fryberg, Praroman; Otto Göttel; Thomas Stauner, both of Marly, all of Switzerland

[73] Assignee: Ilford A.G., Fribourg, Switzerland

[*] Notice: The term of this patent shall not extend beyond the expiration date of Pat. No. 5,686,222.

[21] Appl. No.: 736,599

[22] Filed: Oct. 24, 1996

Related U.S. Application Data

[63] Continuation of Ser. No. 342,207, Nov. 18, 1994, abandoned.

[30] Foreign Application Priority Data

May 24, 1994 [GB] United Kingdom .................. 9410425

[51] Int. Cl.$^6$ .................................................. G03C 1/295
[52] U.S. Cl. ........................................ 430/264; 430/598
[58] Field of Search ...................................... 430/264, 598

[56] References Cited

U.S. PATENT DOCUMENTS

| | | | |
|---|---|---|---|
| 2,419,975 | 5/1947 | Trivelli et al. | |
| 4,269,929 | 5/1981 | Nothnagle | 430/264 |
| 4,459,347 | 7/1984 | Parton et al. | 430/217 |
| 4,668,605 | 5/1987 | Okutsu et al. | 430/267 |
| 4,686,167 | 8/1987 | Resnick et al. | 430/264 |
| 4,740,452 | 4/1988 | Okutsu et al. | 430/439 |
| 4,798,780 | 1/1989 | Hall et al. | 430/264 |
| 4,950,578 | 8/1990 | Yagihara et al. | 430/264 |
| 4,977,062 | 12/1990 | Yagihara et al. | 430/264 |
| 4,994,365 | 2/1991 | Looker et al. | 430/598 |
| 4,997,980 | 3/1991 | Resnick et al. | 564/27 |
| 5,006,445 | 4/1991 | Yagihara et al. | 430/264 |
| 5,013,844 | 5/1991 | Rüger | 546/332 |
| 5,085,971 | 2/1992 | Katoh et al. | 430/264 |
| 5,104,769 | 4/1992 | Looker et al. | 430/264 |
| 5,126,227 | 6/1992 | Machonkin et al. | 430/264 |
| 5,139,921 | 8/1992 | Takagi et al. | 430/264 |
| 5,200,298 | 4/1993 | Takagi et al. | 430/264 |
| 5,212,045 | 5/1993 | Koga et al. | 430/264 |
| 5,279,919 | 1/1994 | Okamura et al. | 430/264 |
| 5,284,732 | 2/1994 | Nii et al. | 430/264 |
| 5,288,590 | 2/1994 | Kuwabara et al. | 430/264 |
| 5,316,889 | 5/1994 | Sakai | 430/264 |
| 5,316,890 | 5/1994 | Okamura et al. | 430/264 |
| 5,378,578 | 1/1995 | Hoshimiya et al. | 430/264 |

FOREIGN PATENT DOCUMENTS

| | | |
|---|---|---|
| 0 598 315 A1 | 5/1994 | European Pat. Off. . |
| 62-211647 | 9/1987 | Japan . |

OTHER PUBLICATIONS

Research Disclosure 36544, pp. 500–541, Sep. 1994.
Yule, J.A.C., *Journal of the Franklin Institute*, pp. 221–230, Mar. 1945.
Okamura et al., *Chemistry of Dir–Hydrazides and Micro–Area Inhibition Technology*, East–West IS&T Meeting Nov. 11, 1992.
Shinohara et al., The *Journal of Photographic Science*, vol. 35, pp. 181–190, Aug. 13, 1987.
Research Disclosure 235, pp. 346–352, Nov. 1983.

*Primary Examiner*—Richard L. Schilling
*Attorney, Agent, or Firm*—Darby & Darby

[57] ABSTRACT

This subject invention relates to novel dihydrazide compounds useful as dot-promoting agents in photographic image systems, methods for making them, and to photographic materials which comprise these compounds.

27 Claims, No Drawings

DIHYDRAZIDES

This is a continuation of application Ser. No. 08/342,207, filed Nov. 18, 1994 now abandoned.

FIELD OF THE INVENTION

This subject invention relates to novel dihydrazide compounds useful as dot-promoting agents in photographic image systems, to methods for making them, and to photographic materials which comprise these compounds.

DESCRIPTION OF THE PRIOR ART

Traditionally, the production of high quality halftone dots was obtained with the use of "lith" films and chemistry. These films, used for making halftone and line images were capable of producing extremely high contrast and good image sharpness. Sharpness is quantified in terms of "edge gradient" which is the ratio of change in optical density (Δ) to distance at the boundary between the exposed part and the unexposed part of the photographic image: In general, the higher the edge gradient the sharper the image e.g. the harder the dot. In the case of halftone images such properties contribute to "high dot quality".

Those skilled in the art attribute the formation of hard dots produced with lith materials to the high contrast obtained from "infectious development" as described by Yule, J. Frank. Inst. 239 221 (1945). In fact high contrast has come to be synonymous with high edge gradient.

Although the dot quality delivered from lith materials is excellent, the lith system has serious disadvantages which restrict its utility. As has been recognized, the disadvantages of the lith system include a shortened useful life of the processing chemistry and deterioration of the image quality due to pepper spots, drag streaks, narrow screen range and high dependence on processing.

Many of the acyl hydrazides described in the literature require processing at high pH (typically above pH 11). In most cases, even at pH of 11 or greater an amine booster or, incorporated amine booster, is required to provide acceptable gradation of dot quality in the processed film. The elevated pH can cause several inherent problems in the developer solution. These include the lack of stability of the developer when exposed to atmospheric oxygen and the generation of pepper in the processed film. Additionally, spent or out-of-specification developer may be characterized as hazardous waste by the U.S. Department of Transportation guidelines, on account of its high pH.

Soluble hydrazides can be incorporated into the processing solutions, but if they are to be incorporated into the photographic element, preferably their mobility is reduced. Typically, this can be achieved by incorporating either a ballast group or a functionality that promotes adsorption to the surface of the silver halide grain. The selection of an adsorption-promoting substituent for a phenyl hydrazide is limited however, in that "tightly adsorbed aryl hydrazides are not usually efficient in increasing the contrast in negative-working silver halide emulsion. It is believed that contrast is increased by infectious development and that undue restriction of mobility interferes with the ability of the aryl hydrazides to promote infectious development". Parton, U.S. Pat. No. 4,459,347. The delicate balance necessary to provide adsorptivity to the silver halide grain while still providing adequate solubility, as well as the requirement for chemical stability and inherent activity, place serious constraints upon the design of new aryl hydrazide contrast-enhancing agents.

When groups such as thiourea, thioamide, heterocyclic rings, or urea are used as adsorption-promoting functionalities, the molar concentration of the hydrazide can be reduced by an order of magnitude without loss of activity. This was a significant advantage over the use of mobile (soluble) hydrazides because, at the high concentrations necessary to effect contrast enhancement in a negative emulsion, some hydrazides release sufficient nitrogen to disrupt the ordered array of the photographic element and thereby deteriorate the image quality. Furthermore, diffusion of the mobile hydrazides into the processing chemistry alters the properties of the chemistry with time.

Significantly, although both the mobile hydrazides and the hydrazides provided with an adsorption-promoting moiety substantially increase the contrast of a photographic emulsion, only a selected few of the latter class also provide acceptable dot quality. Undoubtedly, the dual constraints described above, on controlled adsorptivity of the hydrazide and the printing parameters, a process which requires tight control on screen range, severely limit the initially large number of choices of hydrazide derivatives that produce high contrast. Therefore, it follows that these constraints also limit the number of hydrazides that can produce high quality dots since high contrast is a necessary (though not sufficient) factor in producing high-quality dots.

U.S. Pat. No. 2,419,975 represents an early teaching in the art that high-contrast negative photographic characteristics can be obtained by adding hydrazine compounds to photographic emulsions. The art has however long since recognized that the stability and activity of hydrazides can be regulated by direct attachment of a substituted carbonyl-blocking group to the nitrogen. Presently, only a few substituents attached to the acyl-carbonyl group have demonstrated utility in high contrast systems. The most common in the art are hydrogen, carbonyl, alkyl and aryl which in turn can be substituted. Particularly useful as hydrazine blocking groups are o-hydroxymethyl substituted benzoic acid derivatives and derivatives of oxalic acid.

A few recent patents teach that the most efficient hydrazides employ a combination of substituents to balance photographic performance and chemical stability.

Some of these facts have been recognized and subsequently have become part of the state of the art. Groups promoting the adsorption of hydrazides to the silver halide surface have been described in several recent patents. For instance Machonkin (U.S. Pat. No. 5,126,227) discusses the necessity of incorporating in the hydrazide molecule ballasting groups in order to promote activity due to diffusion fastness, Koga et al. (U.S. Pat. No. 5,212,045) teach that increased diffusion fastness is achieved by doubling hydrazide structures via divalent linkage groups (creating dihydrazides including bis-hydrazides).

In order to achieve enhanced contrast and dot quality it has been proposed to combine hydrazides used as contrast promoting agents with a wide variety of amines. These amines are in general called "boosters".

High contrast developing compositions which contain amino compounds as "boosters" and are intended for carrying out development in the presence of a hydrazine compound are also disclosed in U.S. Pat. Nos. 4,668,605 issued May 26, 1987 and 4,740,452 issued Apr. 26, 1988 and in Japanese Patent Publication No. 211647/87 published Sep. 17, 1987. U.S. Pat. No. 4,668,605 describes developing compositions containing a dihydroxyalkyl group of 2 to 10 carbon atoms, and a mercapto compound. The developing compositions of U.S. Pat. No. 4,740,452 contain a contrast-promoting amount of certain trialkyl amines, monoalkyidi-alkanol amines or dialkylmonoalkanol amines. The developing composition of Japanese Patent Publication No 211647/87 contains a dihydroxybenzene developing agent, a sulfite and certain amino compounds characterized by reference to their partition coefficient values. However, the developing compositions of U.S. Pat. Nos. 4,668,605 and 4,740,452 and Japanese Patent Publication No. 211647/87 do not fully meet the needs of the state of the an because they exhibit many disadvantages. One disadvantage is that the high pH required for the developer solution can unfavorably affect the stability of the developer. Another disadvantage is the problem of handling the high pH developer solution. These solutions are corrosive to many metals and, as stated above, solutions having a pH above 12 are classified by the Department of Transportation (DOT) as a hazardous material.

U.S. Pat. No. 4,269,929 describes the use of a very wide variety of amino compounds as contrast-promoting agents for use in developer baths. In particular, it discloses use of amines, such as hydroxylamines, including aliphatic amines, aromatic amines, cyclic amines, mixed aliphatic-aromatic amines, and heterocyclic amines. Primary, secondary and tertiary amines, as well as quaternary ammonium compounds, are included within the broad scope of the disclosure. Use of booster amines has also been disclosed in Looker, U.S. Pat. No. 4,994,365, (EP 0,458,708) where ballasted hydrazides have been described which contain the same structural elements, for instance hydrazides having the structure:

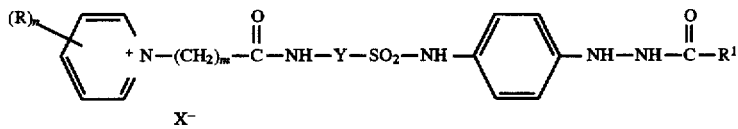

wherein each R is an alkyl group, preferably containing 1 to 12 carbon atoms, n is 1 to 3, X is an anion such as chloride or bromide, m is 1 to 6, Y is a divalent aromatic radical, and $R^1$ is hydrogen or a blocking group. The divalent aromatic radical represented by Y, such as a phenylene radical or naphthalene radical, can be unsubstituted or substituted with one or more substituents such as alkyl, halogen, alkoxy, haloalkyl or alkoxyalkyl.

These hydrazides have been combined with amine boosters of well defined structures added to the coating formulation. Also Machonkin (U.S. Pat. No. 5,126,227) describes improvements to the activity of the combination of hydrazides and boosters by addition to the film of a third compound having the structure:

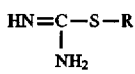

wherein R is alkyl.

While the inventions of U.S. Pat. No. 4,994,365 and U.S. Pat. No. 5,126,227 represent very important technical progress they still suffer from the disadvantage of having to rely on the complex balancing of "incorporated boosters" and additional activity regulators to achieve the necessary activity of the system in an operable pH range.

Some of the disadvantages connected with the addition of amine boosters, either to the processing chemistry or to a coated film, are quite obvious. Some amines are toxic, some have excessive volatility and have highly unpleasant odors, and some tend to form azeotropes with water. Other amines exhibit an inadequate degree of solubility in an aqueous alkaline photographic developing solution, or can have a detrimental affect on the stability of the developer solution and some are costly, yet must be used at a relatively high concentration such that they account for a substantial portion of the total cost of the developing solution. Moreover, a few amines exhibit a degree of activity as contrast-promoters in the method and composition of U.S. Pat. No. 4,269,929 that is less desirable for processing at a pH below about 11.5.

Yagihara (U.S. Pat. No. 4,977,062) (EP 0,286,062) has introduced the concept of "nucleation accelerators". He describes compounds having the structure:

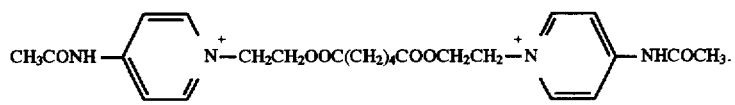

The combination of hydrazides and booster amines in photographic assemblies has been described as "an exceedingly complex system". The proper amount of each component required depends on many parameters such as the concentration of the individual elements as well as the ratio of the different hydrazide/booster combinations. Further, the proper amounts may depend on pH, temperature and time of photographic processing. Precise control of the system and of the processing can become quite difficult. In addition, considerable limitations imposed onto today's photographic systems and therefore also on the individual components used in the design of such systems.

One aspect of eminent practical and commercial value of photographic assemblies of this type is the stability of unprocessed film material under quite adverse conditions. Of equal importance is the reliability and consistent photographic performance of the materials. These aspects favor a simple and flexible design.

A mechanism by which hydrazides operate has been proposed by Okamura et al. East-West IS&T Meeting 1993 and by K. L. Shinohara et al. J. Photo. Sci. 35. 181, 1987, but this proposal should be considered only as a theory by which the present inventive entity is not bound. Based on the proposed mechanism, it becomes quite obvious to those skilled in the art that activity and stability of hydrazides and/or the combination of hydrazides and booster amines are difficult to balance, e.g., the more active a compound or a combination of compounds, the less likely that the compound or combination will exhibit good long term stability.

Sufficient activity and stability are often so tightly interconnected that they seem to be mutually exclusive.

Therefore, what is required are hydrazide compounds with improved stability when incorporated into a photographic material and hydrazide compounds which have been optimized with respect to their activity. It is also desirable to keep the systems simple and easy to control. There exists moreover a need for photographic materials, particularly in the field of graphic arts (i.e. in connection with negative-working surface-latent image emulsions), which function in processing systems with high stability under normal working conditions. It has long been recognized that such stable processing solutions, in particular developer solutions, can only be obtained if the pH of such solutions is kept as low as possible, that is in the range of 9.5 to 12.0, preferably in the range of 9.5 to 11.0.

It has been reported (IS & T 46th Annual Conference 1993) that (generally speaking) a major factor in achieving sufficient activity in hydrazide-promoted photographic systems processed at a pH of 10.5 is strictly linked to hydrazide structures where the ballasting group is linked to the aromatic ring connected to the hydrazine via a sulphonamido group. (See Looker, U.S. Pat. No. 4,994,365.) On the other hand hydrazides of the following general structure have been reported to have high activity;

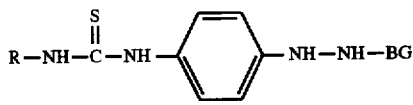

For example, in U.S. Pat. No. 4,686,167 (Resnick et al.); wherein BG is a "blocking group" and R may represent a ballasting group; or

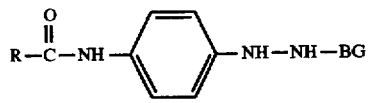

in U.S. Pat. No. 5,279,919 (Hisashi et al.) wherein BG is a blocking group and R represents a ballasting group. In many cases when the ballasting group contains bulky organic substituents for control of diffusion of the molecules the activity-to-weight ratio becomes unfavorable.

In other cases R indicates a group which promotes adhesion to the silver halide surface. Such examples can for instance be found in U.S. Pat. No. 5,085,971 (EP 0,398,285), U.S. Pat. No. 5,200,298, (EP 0,397,167), U.S. Pat. No. 5,006,445 and U.S. Pat. No. 4,686,167. One way to avoid bulky, hydrophobic ballasting groups is to join two hydrazide moieties. Published German Pat. Appln. 2,635,317 discloses compounds joined via a thiourea function. A more recent patent to Koga et al. (U.S. Pat. No. 5,212,045) also describes the possibility of "bridging" the hydrazide structures with a variety of groups of different structures. Most of the compounds described tend to show poor activity due to the lack of activating groups or the lack of efficient silver-complexing centers in the molecule. Therefore, in practice, they can only be used at a pH of about 12. Several of the more recent patents describe structures where the ballasting group is positively charged. These groups are said to promote adhesion of the hydrazides to the silver halide leading to better activity. Hydrazides with high activity, showing little or no diffusion during action, that perform their function close to the silver halide grain, are of particular importance when the photographic material is to be used with modem electronic scanners and image setters which use lasers to generate ultra fine dots (i.e. dots in the 5 μm to 50 μm diameter range). It is, however, well known that an ultra high contrast (i.e. having a gamma greater than about 8, preferably at least 10) photographic material alone is not sufficient to ensure smooth high quality dots in halftone photographic materials. Even hydrazides having high activity at low pH, but lacking diffusion fastness tend to promote dots with ragged edges leading to unsharp images.

The possibility of using either of the above known structures, possibly together with other structural elements to judiciously adjust the activity via specific activating groups and ultimately to achieve an optimized balance between activity, dot quality, activity to weight ratio and hydrazide stability has not been recognized and exploited so far.

The present invention is directed to new diffusion-fast dihydrazides of high activity and high stability corresponding to structures described in the following summary. The invention is also directed to photographic materials containing such dihydrazides.

The present invention is also directed to a method for producing high quality dot images that solves most of the problems inherent in the lith system. The method involves the use of novel dihydrazide derivatives as additives to silver halide emulsions for the purpose of providing good dot quality. However, the invention is not limited to lith-type systems and the present dihydrazides can be used for all purposes for which hydrazines or hydrazides have been found to provide an advantage, e.g., in hybrid-type systems in which hydrazides are incorporated in the so-called "rapid access" photographic materials.

OBJECTS OF THE INVENTION

An object of the invention is to provide novel dihydrazide compounds which act as contrast-enhancing agents that can be used in photographic assemblies to produce high contrast, i.e. wherein γ will be greater than about 8, negative images and provide sufficient activity without requiring a booster amine, (although a booster amine could be added if desired.)

A further object of the present invention is to provide hydrazides with high activity, i.e. hydrazides which possess the ability to generate negatives having high gradation under low-pH development conditions, and display long-term stability when incorporated into photographic assemblies.

Another object of the present invention is to produce a photographic element that can be processed in a stable developer having a pH <11 and still yielding a high contrast material.

Furthermore it is an object of the present invention to provide a photographic element which exhibits reduced pepper grain on development.

In particular the presence of these compounds in photographic silver halide material facilitates the process of forming a high contrast image which permits the production of dot and line images possessing high image quality when exposed in graphic arts cameras or when exposed by electronic scanners, film plotters, image setters using lasers or other high intensity light sources for exposure.

SUMMARY OF THE INVENTION

All patents, patent applications, and literature references cited in the specification are hereby incorporated by reference in their entirety. In the case of inconsist-encies, the present disclosure, including definitions, will prevail.

According to the present invention there are provided hydrazide compounds of the general formula:

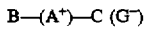

where B and C are the same or different and both have the general formula I:

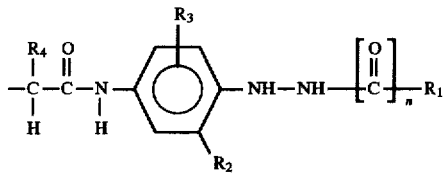

where $R_1$ is hydrogen, alkyl, alkoxy or a blocking group selected from the group consisting of:

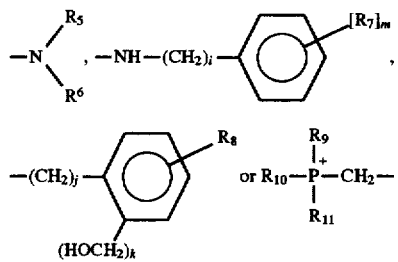

wherein $R_5$ and $R_6$ each are independently selected from the group consisting of hydrogen, alkyl, aminoalkyl, alkylaminoalkyl, acylaminoalkyl, alkylsulphonylaminoalkyl, arylsulphonylaminoalkyl, trialkylammoniumalkyl, hydroxyalkyl, haloalkyl, cycloalkyl, alkoxyalkyl, polyethyleneoxy, aryl, aralkyl, heterocyclic, and wherein $R_5$ and $R_6$ taken together can form a saturated, or partially unsaturated ring containing 3–10 atoms (and optionally containing additional hetero atoms).

$R_7$ and $R_8$ are independently selected from the group consisting of hydrogen, alkyl, aralkyl, hydroxy, alkoxy, haloalkoxy, aryloxy, aralkoxy, hydroxyalkyl, acylamino, sulphonylamino, phenoxy, alkoxyalkoxy, and halogen;

$R_9$, $R_{10}$ and $R_{11}$ are independently alkyl, phenyl or substituted phenyl and where $R_9$ and $R_{10}$ taken together can form a ring;

wherein $R_2$ and $R_3$ are independently hydrogen, alkyl, alkoxy, hydroxyalkyl, aralkyl, aralkoxy and halogen; and $R_2$ and $R_3$ taken together can form a saturated or unsaturated carbocyclic ring; and $R_4$ is hydrogen, alkyl or substituted alkyl; and wherein i, j and k are independently zero or 1.

Without limitation, the alkyl groups can have from 1 to about 18 carbon atoms, the cycloalkyl groups can have from 3 to about 18 carbon atoms, and the aryl groups can have from 6 to about 18 carbon atoms. The preferred alkyl groups can have from 1 to about 10 carbon atoms, the preferred cycloalkyl groups can have from 3 to about 10 carbon atoms and the preferred aryl groups can have from 6 to about 10 carbon atoms. The most preferred alkyl, groups can have found 1 to about 6 carbon atoms, the most preferred cycloalkyl groups can have from 3 to about 6 carbon atoms and the preferred aryl groups will have from 6–8 carbon atoms.

In the compounds of the invention, the preferred cycloalkyl and heterocyclic groups will have from 5, 6 or 7 ring atoms. The most preferred cycloalkyl or heterocyclic group will have 5 or 6 ring atoms.

Without limitation:

the alkyl groups in $R_2$, $R_3$, $R_4$, $R_7$, $R_8$, $R_9$, $R_{10}$ and $R_{11}$ can have from 1 to about 12 carbon atoms; the aryl groups in $R_2$, $R_3$, $R_4$, $R_7$, $R_8$, $R_9$, $R_{10}$ and $R_{11}$ can have from 6 to about 12 carbon atoms;

the carbocyclic and heterocyclic groups in $R_2$, $R_3$, $R_4$, $R_7$, $R_8$, $R_9$, $R_{10}$ and $R_{11}$ can have from 3 to about 12 ring atoms. Preferably the alkyl groups will have from 1 to about 8 carbon atoms, the aryl groups will have from 6 to about 8 carbon atoms and the carbocyclic and heterocyclic groups will have from 3 to about 8 ring atoms. The most preferred alkyl groups will have from about 1 to about 4 carbon atoms.

G is a monovalent anion. Preferably the anion is selected from bromide, chloride, thiocyanate, tosylate or mesylate, n is 1 or 2, i is 0 or 1, j is 0 or 1, and m is 0, 1 or 2.

The activity regulating group, $A^+$, is a cationic regulating group which because of its charge will activate the hydrazide to be functional at a pH below 11.

The activity regulating group, $A^+$ is best described with the following general structures:

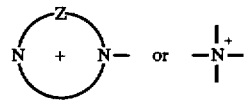

where Z denotes the elements necessary to form a positively charged unsaturated or partially unsaturated 5-membered heterocyclic ring; and the remaining two valences in the single quaternary nitrogen atom can form a ring or are satisfied by groups such as $R_5$ and $R_6$.

Preferably the activity regulating group $A^+$ has the formula II:

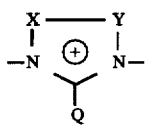

where X and Y denote the atoms necessary to complete an unsaturated or partially unsaturated 5 membered heterocyclic ring, and Q is hydrogen or a ballasting group. The ballasting group is a group which can control the rate of diffusion of the hydrazide thereby enhancing its selectivity. Without limitation, examples of ballasting groups include, hydrogen, methyl, ethyl, propyl, butyl, pentyl, hexyl, heptyl, octyl, phenyl, furyl, thienyl, and the like.

The most preferred structure for $A^+$ is an imidazolium ring or a triazolium ring.

In a preferred embodiment B is the same as C and the hydrazides have the formula III:

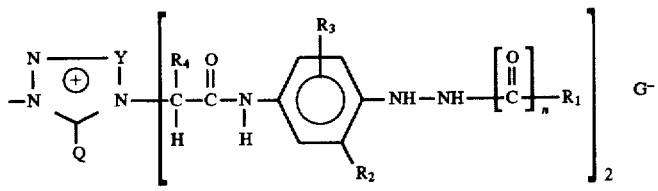

wherein $R_1$, $R_2$, $R_3$, $R_4$ and G are as defined above and the ballasting group, Q, is hydrogen, alkyl, polyethyleneoxy, aryl or a heterocyclic group. Preferably in formula III, Q is an alkyl group having from 1 to about 12 carbon atoms, aryl group having from 6 to about 12 carbon atoms or a heterocyclic group, having from 3 to about 12 ring atoms. In a preferred embodiment Q is an alkyl group having from 1 to 8 carbon atoms, an aryl group having from 6 to 8 carbon atoms, or a heterocyclic group having from 3 to 8 ring atoms.

Preferably in formula III, $R_4$ is hydrogen or methyl.

In one embodiment the blocking group, $R_1$, has formula IV:

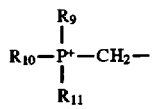

wherein $R_9$, $R_{10}$ and $R_{11}$ are alkyl, substituted alkyl wherein each of the groups have from 1 to about 8 carbon atoms, phenyl, or substituted-phenyl wherein each of the groups have from 6 to about 8 carbon atoms, or cyanoethyl and n is 1.

Preferably in formula IV $R_9$, $R_{10}$ and $R_{11}$ are alkyl groups having 1 to 4 carbon atoms, or are each phenyl, tolyl, or cyanoethyl.

Preferably in the hydrazides of formula I, $A^+$ has formula II and $R_2$ and $R_3$ are independently hydrogen, methyl, ethyl, methoxy, ethoxy, hydroxyethyl, chlorine or fluorine.

Most preferably $R_2$ and $R_3$ are each hydrogen, methyl or methoxy.

In another embodiment of the hydrazides of the invention, the blocking group $R_1$ has the formula V:

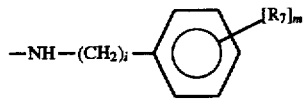

wherein $R_7$ is hydrogen, hydroxy, alkyl, alkoxy, haloalkoxy, halogen, methoxyalkoxy or hydroxyalkoxy and n is 2 and m is zero, 1 or 2. In a preferred embodiment $R_1$ is an 2-hydroxyanilyl group.

Preferably when $R_1$ has formula V, $R_7$ is hydrogen, hydroxy, methyl, ethyl, methoxy, ethoxy, hydroxyethyl, hydroxymethyl, chlorine or fluorine, n (from Formula I) is 2, and m is 1 or 2.

In a further embodiment of the hydrazides of the invention, the blocking group $R_1$ has the formula VI:

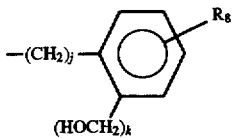

wherein $R_8$ is hydrogen, halogen, alkoxy, alkyl, acylamino or sulphonylamino, j is zero, 1 or 2 and n is 1. In a preferred embodiment the alkyl groups can have from 1 to about 10 carbon atoms, the acylamino groups can have from 1 to about 10 carbon atoms, and the sulphonylamino group can have from 6 to 10 carbon atoms.

In another embodiment of the hydrazides of formula I the blocking group $R_1$ has the formula VII:

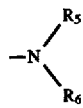

where $R_5$ and $R_6$ are independently selected from the group consisting of hydrogen, alkyl, aminoalkyl, alkylaminoalkyl, acylaminoalkyl, trialkylammoniumalkyl, hydroxyalkyl, cycloalkyl, polyethyleneoxy, phenyl, aralkyl, furfuryl or other heterocyclic groups;

wherein $R_5$ and $R_6$ taken together can form a substituted or unsubstituted heterocyclic ring, and n is 2.

In a preferred blocking group, $R_1$, of formula VII, $R_5$ and $R_6$ are hydrogen or alkyl, hydroxyalkyl, haloalkyl, cycloalkyl, aralkyl wherein each of the groups have from 1 to about 8 carbon atoms or methoxyethyl, or $R_5$ and $R_6$ are taken together to form a heterocyclic ring having from 3 to 6 atoms and n is 2. In a preferred embodiment the $R_5$ and $R_6$ groups can be independently alkyl groups having from 1 to about 8 carbon atoms, cycloalkyl groups having from 3 to 8 carbon atoms or aryl groups having from 6 to about 8 carbon atoms.

Preferably the regulating group $A^+$ of formula II is

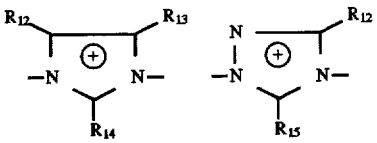

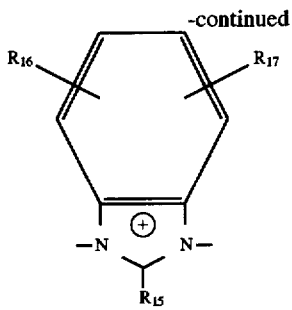

wherein $R_{12}$ and $R_{13}$ are independently hydrogen, or alkyl, alkoxy, or alkoxyalkoxy, aralkyl, aryl, aralkoxy, or halogen.

$R_{14}$ and $R_{15}$ are independently hydrogen, or alkyl, alkoxy, acylamino or alkylthio wherein each of the groups have 1 to about 8 carbon atoms, aralkyl, aryl, aryloxy, heterocylic or arylthio.

$R_{16}$ and $R_{17}$ are independently hydrogen or alkyl, alkoxy, alkoxylalkyl, or aralkoxy, aryl, or halogen.

In a preferred embodiment:

$R_{12}$ and $R_{13}$ are hydrogen, or alkyl, substituted alkyl, alkoxy, or alkoxyalkoxy, wherein each of the groups have from 1 to about 8 carbon atoms, aralkyl, aryl, aralkoxy, wherein each of the groups have from 6 to 8 carbon atoms, or halogen;

$R_{14}$ and $R_{15}$ are independently hydrogen, or alkyl, alkoxy, acylamino or alkylthio wherein each of the groups have 1 to about 8 carbon atoms, aralkyl, aryl, aryloxy, or arylthio wherein each of the groups have from 6 to 8 carbon atoms; and $R_{16}$ and $R_{17}$ are independently hydrogen or alkyl, alkoxy, alkoxylalkyl, wherein each of the groups have from 1 to about 8 carbon atoms or aralkoxy, aryl, wherein each of the groups have from 6 to about 8 carbon atoms, or halogen.

Most preferably $A^+$ of formula II is of the formula VIII:

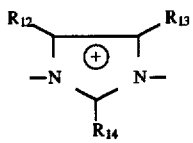

wherein $R_{12}$ and $R_{13}$ are as described above and $R_{14}$ is hydrogen, alkyl, aryl, aralkyl, wherein the preferred aryl groups are tolyl, benzyl or thiophenyl, and wherein alkyl has preferably 1 to 17 carbon atoms.

An especially useful regulating group $A^+$ is the group having the formula IX:

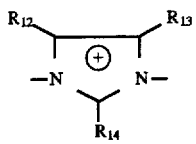

wherein $R_{12}$ and $R_{13}$ are independently hydrogen, ethyl, methyl, ethoxy, or methoxy and $R_{14}$ is hydrogen, an alkyl group having from 1 to about 8 carbon atoms or phenyl.

All of the groups $R_2$ through $R_{17}$ of the invention can optionally be substituted. The substituents include alkyl hydroxy, alkoy, aryl, amino, halo, aryl, aryl, sufonyl, and the like.

A particularly preferred hydrazide of formula I wherein the regulating group $A^+$ is of formula VIII is the hydrazide having the formula X:

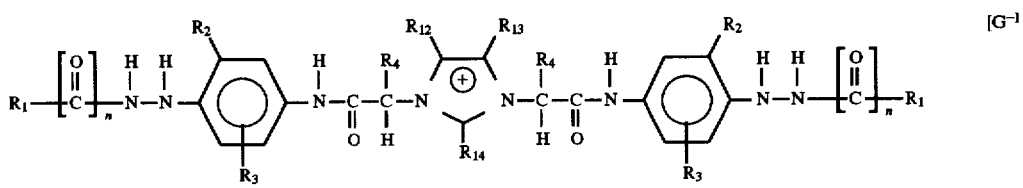

wherein $R_1$, $R_2$, $R_3$, $R_4$, $R_{12}$, $R_{13}$, $R_{14}$, and n are as defined above.

When used in a photographic system the dihydrazides of the subject invention double the contrast γ, over a similar emulsion without dihydrazide compound. When used under the following conditions in a developer at a pH of 10–75, a development time of 35 seconds at a temperature of 35 degrees centigrade.

The following General Synthesis Scheme illustrates the general method for preparing the compounds of the invention. In this scheme the compounds required for the proposed steps are listed in Table 1.

The first step is reaction of ester (C) with hydrazine (D). (Alternatively, when n is 2 an oxalate ester is employed and the resultant product is reacted with an amino compound (E) to produce a semioxamazide.) The nitro group is then reduced with hydrogen and a catalyst to provide an aniline compound. The aniline compound is then reacted with an halide substituted acylhalide or an anhydride (G) to produce a halohydrazide compound. Two equivalents of halohydrazides are then reacted with a aliamine compound (A) to form the dihydrazide. In the General Synthesis Scheme $A^-$ is the activity regulating group, n is 1 or 2.

The compounds used to form the compounds of the invention are also listed in Table 1. These compounds are named in Table 2.

Compounds having different B and C groups are easily formed by reacting one equivalent of halo-haldrazide with one equivalent of an A compound. If any bishydrazide product is formed, this can be readily separated, along with any unreacted A compound, by any suitable method such as chromatography or recrystallization, for example. The resulting monoallcylated compound can then be reacted with a different halo-hydrazide to provide a dihydrazide wherein B and C are different.

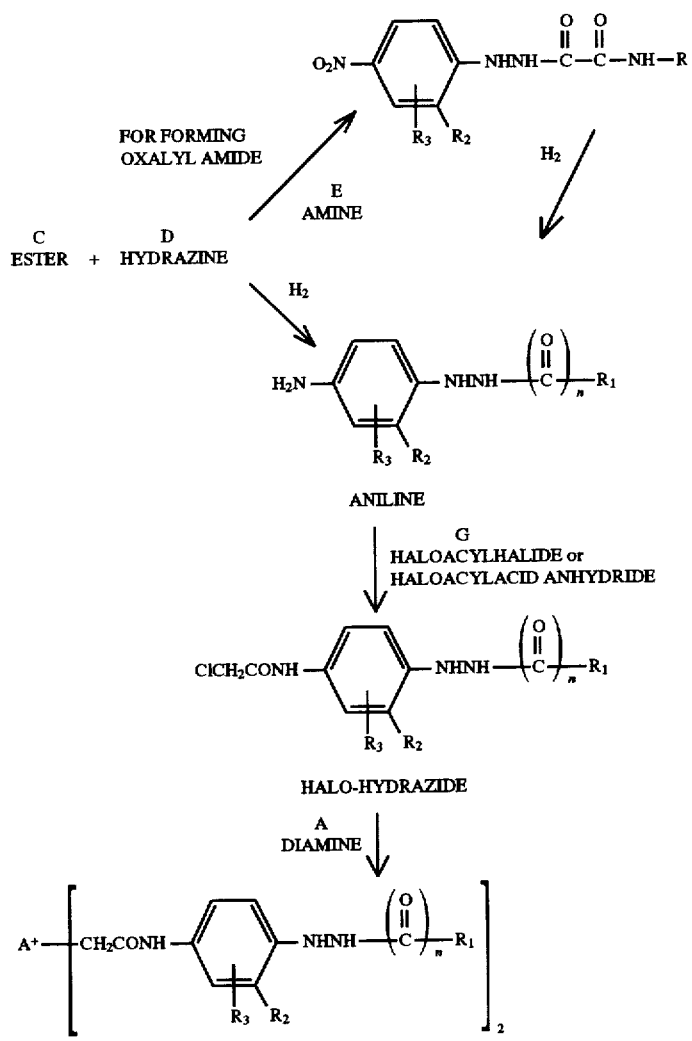
General Synthesis Scheme
ANILINE
HALO-HYDRAZIDE
| COMP. NO. | REACT. C | REACT. D | REACT. E | REACT. G | REACT. A |
|---|---|---|---|---|---|
| 3.01 | C.1 | D.1 | E.1 | G.1 | A.15 |
| 3.02 | C.1 | D.1 | E.4 | G.1 | A.1 |
| 3.03 | C.1 | D.1 | E.1 | G.1 | A.16 |
| 3.04 | C.1 | D.1 | E.3 | G.1 | A.15 |
| 3.05 | C.1 | D.1 | E.1 | G.1 | A.23 |
| 3.06 | C.1 | D.1 | E.1 | G.1 | A.17 |
| 3.07 | C.2 | D.1 | — | G.1 | A.1 |
| 3.08 | C.5 | D.2 | — | G.1 | A.1 |
| 3.09 | C.4 | D.2 | — | G.1 | A.1 |
| 3.10 | C.1 | D.1 | E.1 | G.1 | A.18 |
| 3.11 | C.1 | D.1 | E.1 | G.1 | A.19 |
| 3.12 | C.1 | D.1 | E.1 | G.1 | A.1 |
| 3.13 | C.1 | D.3 | E.1 | G.1 | A.19 |
| 3.14 | C.1 | D.1 | E.2 | G.1 | A.1 |
| 3.15 | C.1 | D.4 | E.2 | G.1 | A.1 |
| 3.16 | C.1 | D.2 | E.2 | G.1 | A.1 |
| 3.17 | C.1 | D.1 | E.5 | G.1 | A.1 |
| 3.18 | C.1 | D.1 | E.5 | G.1 | A.2 |
| 3.19 | C.1 | D.2 | E.1 | G.1 | A.1 |
| 3.20 | C.1 | D.2 | E.3 | G.1 | A.2 |
| 3.21 | C.1 | D.2 | E.3 | G.1 | A.1 |
| 3.22 | C.1 | D.1 | E.6 | G.1 | A.1 |
| 3.23 | C.1 | D.1 | E.6 | G.1 | A.3 |
| 3.24 | C.1 | D.1 | E.6 | G.1 | A.2 |
| 3.25 | C.1 | D.1 | E.7 | G.1 | A.1 |
| 3.26 | C.1 | D.1 | E.8 | G.1 | A.3 |
| 3.27 | C.1 | D.1 | E.8 | G.1 | A.2 |
| 3.28 | C.1 | D.1 | B.9 | G.1 | A.1 |
| 3.29 | C.1 | D.1 | E.3 | G.1 | A.1 |
| 3.30 | C.1 | D.1 | E.3 | G.1 | A.2 |
| 3.31 | C.1 | D.1 | E.1 | G.1 | A.2 |
| 3.32 | C.1 | D.2 | E.2 | G.1 | A.2 |
| 3.33 | C.1 | D.1 | E.10 | G.1 | A.3 |
| 3.34 | C.1 | D.1 | E.10 | G.1 | A.15 |
| 3.35 | C.1 | D.2 | — | G.1 | A.2 |
| 3.36 | C.1 | D.1 | E.2 | G.1 | A.2 |
| 3.37 | C.3 | D.2 | — | G.1 | A.19 |
| 3.38 | C.3 | D.2 | — | G.1 | A.1 |
| 3.39 | C.3 | D.2 | — | G.1 | A.2 |
| 3.40 | C.3 | D.2 | — | G.1 | A.21 |
| 3.41 | C.1 | D.1 | E.1 | G.1 | A.22 |
| 3.42 | C.3 | D.2 | — | G.1 | A.24 |

TABLE 1-continued

| COMP. NO. | REACT. C | REACT. D | REACT. E | REACT. G | REACT. A |
|---|---|---|---|---|---|
| 3.43 | C.3 | D.2 | — | G.1 | A.25 |
| 3.44 | C.1 | D.2 | E.11 | G.1 | A.1 |

TABLE 2

| | |
|---|---|
| C.1 | diethyl oxalate |
| C.2 | ethyl formate |
| C.3 | phthalide |
| C.4 | ethyl acetate |
| C.5 | ethyl 4-methylbenzoate |
| D.1 | 2-methyl-4-nitrophenylhydrazine |
| D.2 | 4-nitrophenylhydrazine |
| D.3 | 2-methyl-5-methoxy-4-nitrophenylhydrazine |
| D.4 | 2-methoxy-4-nitrophenylhydrazine |
| E.1 | methyl amine |
| E.2 | 2-hydroxyethyl amine |
| E.3 | 2-methoxyethyl amine |
| E.4 | n-octyl amine |
| E.5 | benzyl amine |
| E.6 | ethyl amine |
| E.7 | n-nonyl amine |
| E.8 | n-butyl amine |
| E.9 | furfuryl amine |
| E.10 | 1-amino-3-methoxypropane |
| E.11 | 2-hydroxyaniline |
| E.12 | 2-hydroxy-4-methylaniline |
| G.1 | chloroacetyl chloride |

TABLE 2-continued

| | |
|---|---|
| G.2 | 4-chloromethylbenzoyl chloride |
| A.1 | 2-ethyl imidazole |
| A.2 | 2-butyl imidazole |
| A.3 | 2-propyl imidazole |
| A.4 | 1,4-diazabicyclo[2,2,2]octane |
| A.5 | 1,4-dimethylpiperazine |
| A.6 | N,N,N,-tetramethylethylenediamine |
| A.7 | N,N,N,-tetramethyl-1,4-phenylenediamine |
| A.8 | 4-4'-dipyridyl |
| A.9 | 4,4'-trimethylenedipyridine |
| A.10 | 4-4'-dipyridyl thioether |
| A.11 | 4-4'-dipyridyl ether |
| A.12 | 4,4'-dimethylaminophenyl ether |
| A.13 | 4,4'-dimethylaminophenyl thioether |
| A.14 | N,N'-tetramethylenediimidazole |
| A.15 | 2-heptyl imidazole |
| A.16 | 2-methyl-5,6-dimethoxybenzimidazole |
| A.17 | benzimidazole |
| A.18 | imidazole |
| A.19 | 2-methyl imidazole |
| A.20 | 2-pentyl imidazole |
| A.21 | 2-phenyl imidazole |
| A.22 | triazole |
| A.23 | 2-ethyl-4-methyl imidazole |
| A.24 | 2-thienyl imidazole |
| A.25 | 2-furyl imidazole |

Synthesis of Compound 3.12

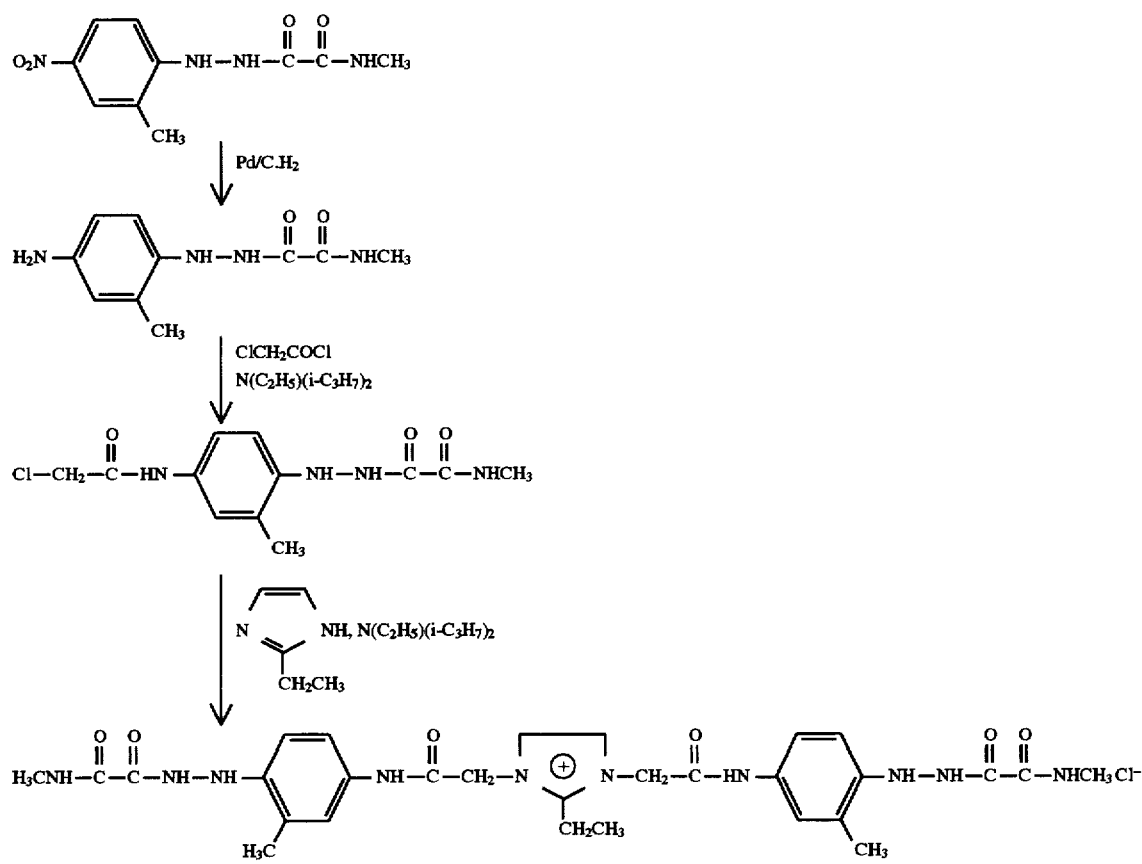

Synthesis of Compound 3.12
STEP A

A mixture of 126.1 g of methylaminoxalyl-2-(2-methyl-4 nitrophenyl) hydrazide, 125 ml of methylcellosolve and 10% Pd/C catalyst was hydrogenated at 50 psi over a 20 hour period to provide the corresponding aniline. Then the reaction mixture was heated briefly on a steam bath and the catalyst was filtered off. On cooling the product precipitated in the form of yellowish needles. Yield: 97.8 g.

STEP B

A solution of 44.5 g of the aniline compound prepared in step A and 28.5 g of N,N-diisopropylethylamine in 220 ml of dry dimethylacetamide was cooled and maintained at 0° C. in an ice bath. 23.7 g of chloroacetylchloride was added over a 30 minute period. The reaction mixture was stirred at room temperature for 2 hours. Then the reaction mixture was poured into ice water the separated solid was filtered off, washed with water and dried. The anilide product was a colorless solid. Yield: 54.9 g.

Compound 3.12

A solution of 6 g of the anilide compound prepared in step B, 0.96 g 2-ethylimidazole and 1.3 g of N,N-diisopropyl-ethylamine in 15 ml N,N-dimethylacetamide was heated to 120° C. After 3 hours the reaction mixture was cooled to 80° C. and then poured into 100 ml of isopropanol. The suspension formed was allowed to cool to room temperature with stirring. The colorless product was filtered off, washed with isopropanol, and dried—Yield: 4.8 g.

The structure agrees with the expected nmr spectrum.

Synthesis of Compound 3.06
STEP A

A mixture of 126.1 g of methylamino oxalyl-2-(2'-methyl-4'-nitrophenylhydrazide, 125 ml of methylcellosolve and 10% Pd/C catalyst was hydrogenated at 50 psi over a 20 hour period to the corresponding aniline. Then the reaction mixture was heated up briefly on a steam bath and the catalyst was filtered off. On cooling the product precipitated in yellowish needles. Yield: 97.8 g.

STEP B

A solution of 44.5 g of the aniline from Step A, and 28.5 g of N,N-disopropylethylamine in 220 ml of dry dimethy-lacetamide was cooled in an ice bath. 23.7 g of chloroace-tylchloride was added over a 30 minute period of 0° C. The reaction mixture was stirred at room temperature for 2 hours. Then the reaction mixture was poured into ice water; the separated solid was filtered off, washed with water and dried. The halo-hydrazide product was a colorless solid, 54.9 g.

Compound 3.06

A solution of 6 g of the halohydrazide from Step B, 1.2 g of benzimidazole and 1.3 g of N,N-diisopropyl-ethylamine in 15 ml N,N-dimethylacetamide was heated up to 120° C. After 3 hours the reaction mixture was cooled to 80° C. and then poured into 100 ml of isopropanol. The suspension thus formed was allowed to cool to room temperature while stirring. The yellowish product was filtered off, washed well with isopropanol and dried; 4.6 g.

The structure agrees with the nmr spectrum.

Synthesis of Compound 3.21
STEP A

The synthesis of ethoxalyl-2-(4-aminophenyl) hydrazide is described in U.S. Pat. No. 4,997,980.

STEP B 22.3 g of ethoxalyl-2-(4-aminophenyl) hydrazide and 9 g of 2-methoxyethylamine is heated up to reflux in 200 ml of methanol over 1 hour. The reaction mixture is cooled to room temperature and the solid is filtered off and washed with cold methanol. A light colored solid, 21.9 g was obtained.

STEP C

The chloroacetylation follows the procedure described above in the synthesis of Compound 3.06.

Compound 3.21

The final step follows the procedure as described in the final step for compound 3.06 but ethylimidazole was used instead of benzimidazole.

The structure agrees with the nmr spectrum.

Synthesis of Compound 3.38

To a solution of 60 g of 2-(4-aminophenyl)-1-(2-hydroxymethylbenzoyl)hydrazine in 225 ml of (N-methyl-2-pyrrolidinone (NMP) was added a solution of 41 g of chloroacetic anhydride in 80 ml of NMP at room temperature during a period of 1 hour. Stirring was continued for another 2 hours and a mixture of 550 ml of water and 150 ml of isopropanol was slowly poured into the reaction mixture. The precipitate was filtered and washed with water. After recrystallization from 1 liter of ethanol and drying in a vacuum oven at 60° C., 47 g (61% of theoretical) of the 2-(4-chloroacetylaminophenyl)-1-(2-hydroxymethylbenzoyl)-hydrazine (i.e. the halohydrazide) in the form of white crystals were obtained, m.p. 172°–173° C.

Compound 3.38

A mixture of 16.7 g of the 2-(4-Chloroacetylamino-phenyl)-1-(2-hydroxymethylbenzoyl) hydrazine, 2.4 g of 2-ethylimidazole, 12.9 g of N,N-diisopropylethylamine and 40 ml of N,N-dimethylacetamide was heated to 115° C. for 4 hours. After cooling to room temperature the reaction mixture was poured into 500 ml of cold water. The precipitate was filtered and the slightly moist product suspended twice in 500 ml of ethylacetate. After treating the crystals with 500 ml of ether the product was collected on a filter and dried in a vacuum oven at 40° C. 9.1 g (50% of theoretical) of a nearly colorless product were obtained.

The structure agrees with the expected nmr spectrum.

Compound 3.41

A solution of 6 g of the halohydrazide from Step B of compound 3.06 described above and 0.9 g of sodium 1,2,4-triazole was heated up in 15 ml N,N-dimethylacetamide to 120° C. After 4 hours the reaction mixture was cooled to room temperature, filtered and then poured into 100 ml of isopropanol. The suspension thus formed was stirred for 1 hour. The slightly yellowish product was filtered off, washed well with isopropanol, and dried; 4.4 g.

The structure agrees with the mnr spectrum.

Specific examples of compounds represented by the general formula 1 are given below in Table 3 but the present invention is not limited to these examples.

The aryl hydrazides or the corresponding chlorohydrates were prepared by various methods. A good overview is given in 'Methoden der Organischen Chemie', (Houben Weyl), 4th edition, volume X/2. Particularly suitable therein is the reduction of aryl diazonium salts with tin (II) chloride in the presence of hydrochloric acid (pages 201 ff).

The conversion into the β-formyl compounds is described in the same volume (page 355). The method for the preparation of further β-acyl hydrazines is the hydrazinolysis of carboxylic acid esters (same volume, pages 355ff), anhydrides (pages 357f), acid chlorides (pages 358f) or the reaction of the aryl hydrazine with carboxylic acids and dicyclohexyl carbodiimide (page 355). The synthesis of oxalic acid hydrazides is as described in U.S. Pat. No. 4,997,980.

Specific examples of compounds represented by the general formula I are given below in Table 3 but the present invention is not limited to these examples.

The reagents required for the synthesis of the compounds of the invention are readily available from a number of commercial sources such as Aldrich Chemical Co. (Milwaukee, Wis., U.S.A.); Sigma Chemical Co. (St. Louis, Mo., U.S.A.); and Fluka Chemical Corp. (Ronkonkoma, N.Y., U.S.A.); Alfa Aesar (Ward Hill, Mass. 01835-9953); Eastman Chemical Company (Rochester, N.Y. 14652-3512); Lancaster Synthesis Inc. (Windham, N.H. 03087-9977); Spectrum Chemical Manufacturing Corp. (Janssen Chemica) (New Brunswick, N.J. 08901); Pfaltz and Bauer (Waterbury, Conn. 06708).

Compounds which are not commercially available can be prepared by employing known methods from the chemical literature. For example, compounds II.1, II.3 and II.4 can be prepared by following the procedure in *J. Chem. Soc. Perkin Trans. I*, 16, 1555, (1975). Compound VI.2 can be prepared by following the procedure in J. Organic Chemistry, 39, 1134, (1974). Compound VI. 13 can be prepared by following the procedure in German Off. 1,816,743. Compound VI.14 can be prepared by following the procedure in J. Medic Pharm. Chem, 2, 299, (196). Compound VI. 16 can be prepared by following the procedure in *J. Organic Chemistry*, 24, 1451, (1959).

TABLE 3

TABLE 3-continued
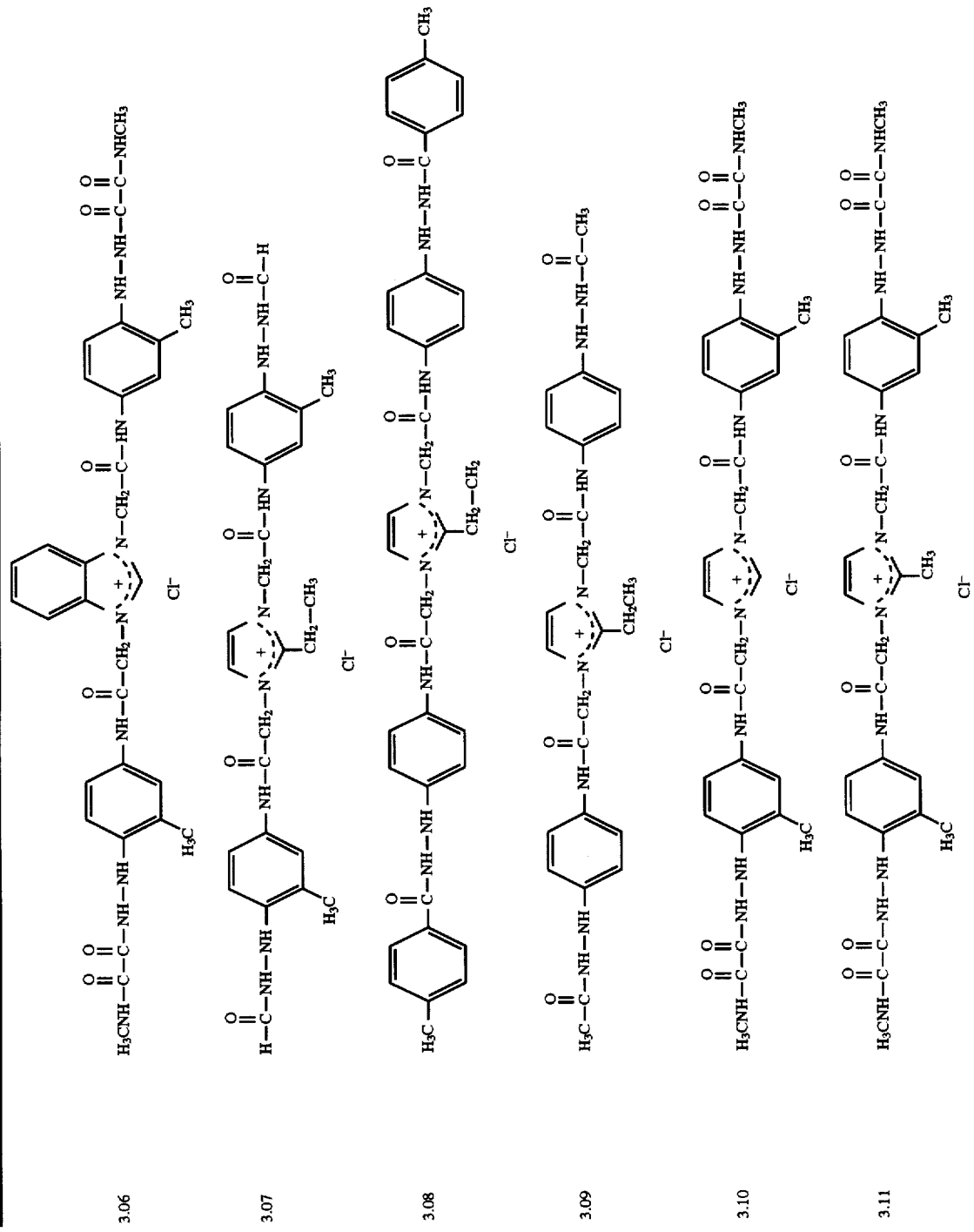

TABLE 3-continued

TABLE 3-continued

TABLE 3-continued
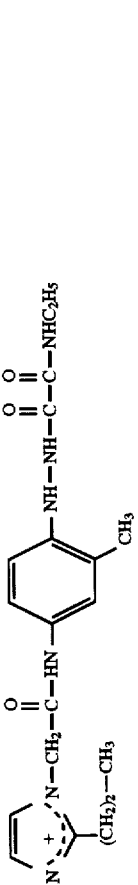

TABLE 3-continued

TABLE 3-continued

| No. | Structure |
|---|---|
| 3.35 | (chemical structure) |
| 3.36 | (chemical structure) |
| 3.37 | (chemical structure) |
| 3.38 | (chemical structure) |
| 3.39 | (chemical structure) |
| 3.40 | (chemical structure) |

TABLE 3-continued
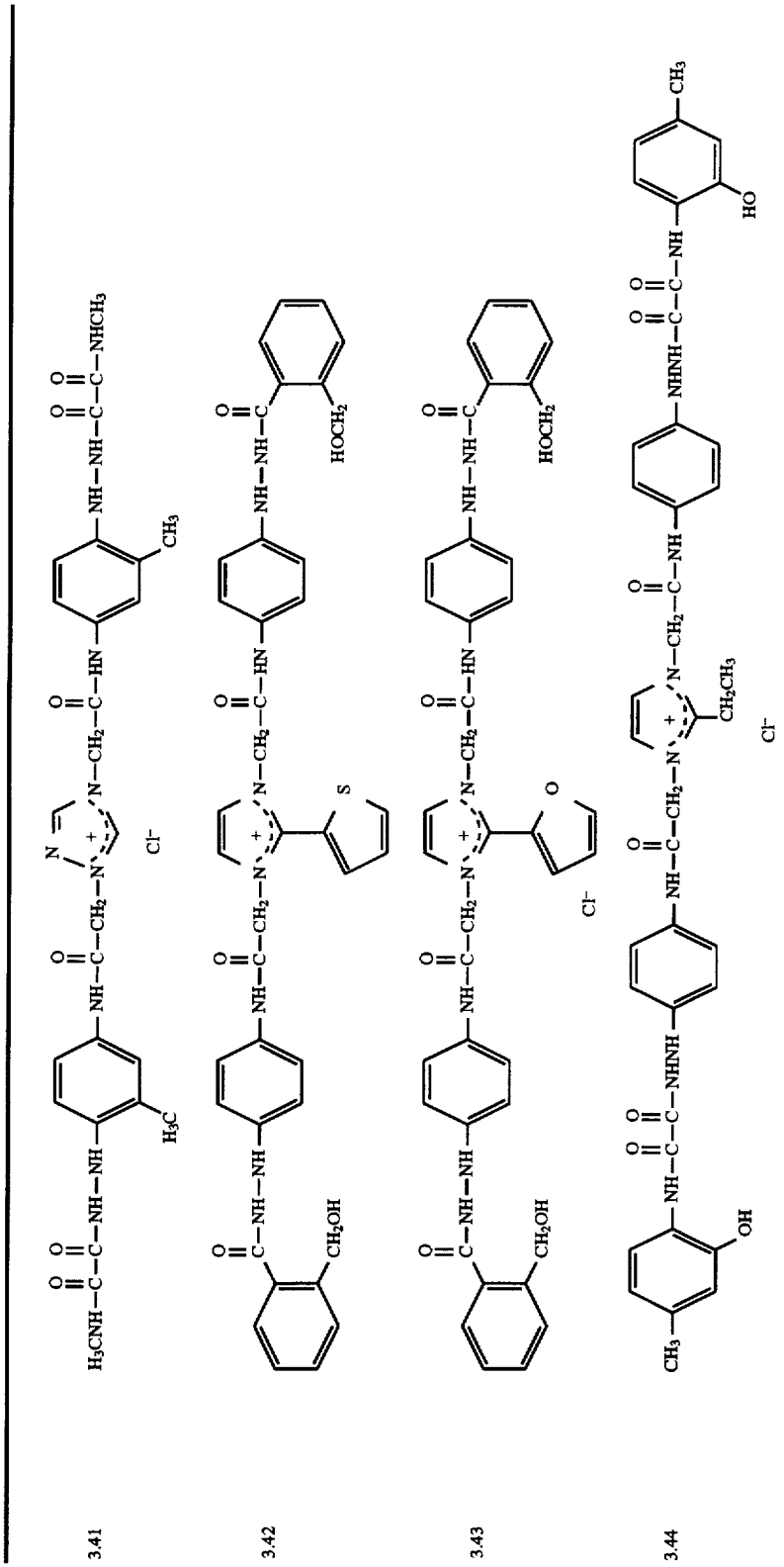
3.41
3.42
3.43
3.44

The amount of the compound of formula (I) added to the silver halide emulsion layer or to another hydrophilic colloid layer(s) of a photographic material is such that the compound does not appreciably function as a developer. Typically, amounts from $10^{-8}$ to $5\times10^{-2}$ moles/mole silver (Ag) and preferably about $10^{-4}$ to $8\times10^{-3}$ moles/mole Ag are used.

The compound can be incorporated in a silver halide emulsion used in the photographic element. Alternatively, the hydrazide compound can be present in a hydrophilic colloid layer of the photographic element, preferably a hydrophilic colloid layer which is coated to be contiguously adjacent to the emulsion layer in which the effects of the compound are desired. The compound of the present invention can, of course, be present in the photographic element distributed between or among the emulsion and hydrophilic colloid layer(s), such as undercoating layers and overcoating layers.

The hydrazide compounds of the present invention are employed in combination with negative-working photographic emulsions comprising radiation-sensitive silver halide grains capable of forming a surface latent image, and a binder. The silver halide emulsions include the high chloride, chlorobromo or chlorobromoiodo emulsions conventionally employed in forming lith photographic elements as well as silver bromide and silver bromoiodide emulsions, which are recognized in the art to be capable of attaining higher photographic speeds. Generally, the iodide content of the silver halide emulsions is less than about 10 mole percent silver iodide, based on the total amount of silver halide.

The compound of formula (I) can be incorporated in the photographic element by common techniques used for the addition of additives to photographic emulsions. The compound is typically dissolved in a solvent selected from water or organic solvents compatible with water, such as alcohols, glycols, ketones, esters, amides, and the like which exert no adverse influences on the photographic characteristics. Then the solution is added to the photographic element. Preferred solvents include dimethylformamide (DMF), dimethylsulfoxide (DMSO), N-methyl-2-pyrrolidinone (NMP) or water.

Alternatively, the compounds of formula (I) can be added to the emulsion as an oil dispersion by known methods used when water-insoluble (so-called oil soluble) couplers are added to emulsions. Preferred oils include N-butyl acetanilide, N-methyl formanilide and N,N-diethyl-m-toluamide. These oils are all commercially available. Ultrasound can be employed to dissolve marginally soluble hydrazides.

Still another way to introduce compounds of formula I is in the form of fine dispersions loaded onto latex particles. Suitable latexes are described below. Hydrazides which are only sparingly soluble in water can be introduced as their water-soluble cyclodextrine complexes. The preferred way for introduction of the claimed hydrazides is as aqueous solutions. Optionally, the compounds may be dissolved in a small amount of organic solvent before the solution is added to water.

These solutions or dispersions can be added to the emulsion at any stage subsequent to the precipitation and washing steps. Preferably, these hydrazide agents should be added just prior to coating.

Examples of latex polymers which can be are useful in practicing the subject invention include polymers composed of one or more alkyl acrylates or methacrylates, acetoacetoxy acrylates and acetacetoxymethacrylates, alkoxyalkyl acrylates or methacrylates, glycidyl acrylates or methacrylates, acryl- or methacrylamide, vinyl esters (for example, vinyl acetate), acrylonitrile, olefins and styrene, etc., and polymers comprising a combination of the above described monomers and acrylic acid, methacrylic acid, 2-sulfoethyl acrylate, vinyl sulfonate, unsaturated dicarboxylic acids, hydroxyalkyl acrylates or methacrylates, or styrenesulfonic acid, etc. For example, those compounds described in U.S. Pat. Nos. 2,376,005, 2,739,137, 2,853,457, 3,062,674, 3,411,911, 3,488,708, 3,525,620, 3,607,290, 3,635,715 and 3,645,740, and British Pat. Nos. 1,186,699 and 1,307,373, all incorporated by reference, can be used. A suitable amount of the polymer latex ranges from about 10 to 80% by weight based on the total weight of the binders. A preferred amount of polymer latex is from about 10% to 40% by weight based on the total weight of the binders. Since high-contrast emulsions such as that used in this invention are suitable for the reproduction of line drawings and the dimensional stability is of importance for such a purpose, it is preferred to use a polymer dispersion, as described above.

Gelatin is advantageously used as a binder or protective colloid in the photographic emulsion, but other hydrophilic colloids can also be used. For example, useful binders include but are not limited to gelatin derivatives, graft polymers of gelatin with other high molecular weight materials, proteins such as albumin or casein, cellulose derivatives such as hydroxyethyl cellulose, carboxymethyl cellulose or cellulose sulfate, saccharide derivatives such as sodium alginate or starch derivatives. The preferred binders are gelatin or a blend of gelatin with a latex polymer.

Also, various synthetic hydrophilic high molecular weight materials such as homopolymers or copolymers, e.g., polyvinyl alcohol, poly-N-vinyl pyrrolidone, polyacrylic acid, polymethacrylic acid, polyacrylamide, polyvinyl imidazole, polyvinyl pyrazole or polyurethane can be added as hydrophilic colloids. Preferred are homo-, co- or terpolymers in the form of latexes having small particle size distribution.

Examples of suitable gelatin graft polymers include those prepared by grafting a homopolymer or a copolymer of a vinylic monomer such as acrylic acid, methacrylic acid, the derivatives thereof (such as the esters or the amides thereof), acrylo-nitrile or styrene to gelatin. Particularly preferred are graft polymers prepared from polymers which are compatible, to some degree, with gelatin, such as polymers of acrylic acid, methacrylamide or a hydroxyalkyl methacrylate. Examples of those polymers are described in, e.g., U.S. Pat. Nos. 2,763,625, 2,831,767 and 2,956,884, etc. Typical synthetic hydrophilic high molecular weight materials are described in, e.g., German Patent Application (OLS) 2,312,708, U.S. Pat. Nos. 3,620,751, and 3,879,205, all incorporated by reference.

In forming photographic elements, the layers can be coated on photographic supports by various procedures, including immersion or dip coating, roller coating, reverse roll coating, doctor blade coating, gravure coating, spray coating, extrusion coating, bead coating, stretch-flow coating and curtain coating. High speed coating using a pressure differential is illustrated in U.S. Pat. No. 2,681,294.

The layers of the photographic elements can be coated on a variety of supports. Typical photographic supports include polymeric films provided with one or more layers to enhance the adhesive, antistatic, dimensional stability, abrasive, hardness, frictional, antihalation and/or other properties of the support surface.

Typical of useful polymeric film supports are polyester films and films of cellulose nitrate and cellulose esters such as cellulose triacetate and diacetate, polystyrene, homo- and copolymers of vinyl chloride, poly(vinyl acetal, polyolefin, particularly a polymer of an olefin containing 2 to 10 carbon atoms, such as polyethylene, polypropylene, copolymers of ethylene and propylene and the like.

Polyolefins, such as polyethylene, polypropylene and copolymers of ethylene with propylene, as illustrated in U.S. Pat. No. 4,478,128, are preferably employed as resin coatings over paper, as illustrated in U.S. Pat. Nos. 3,411,908 and 3,630,740, over polystyrene and polyester film supports, as illustrated by U.S. Pat. No. 3,973,963.

Preferred cellulose ester supports are cellulose triacetate supports, as illustrated in U.S. Pat. Nos. 2,492,977; 2,492,978 and 2,739,069, as well as mixed cellulose ester supports, such as cellulose acetate propionate and cellulose acetate butyrate, as illustrated by U.S. Pat. No. 2,739,070.

Preferred polyester film supports are comprised of linear polyester, such as illustrated in U.S. Pat. Nos. 2,627,088; 2,720,503; 2,779,684 and 2,901,466.

The photographic emulsion used in this invention can be prepared using the well-known methods described in, e.g., P. Glafkides, Chimie et Physique Photographique, Paul Montel, Paris (1967), G. F. Duffin, Photographic Emulsion Chemistry, The Focal Press, London (1966). V. L. Zelikman et al., Making and Coating Photographic Emulsions, the Focal Press, London (1964), all incorporated by reference. These methods include the acidic method, the neutral method, the ammonia method illustrated by Glafkides, Photographic Chemistry, Vol. 1, Fountain Press, London, 1958, pp. 365-368 and pp. 301-304; thiocyanate ripened emulsions, as illustrated by Illingsworth (U.S. Pat. No. 3,320,069); thioether ripened emulsions, as illustrated by McBride (U.S. Pat. No. 3,271,157), Jones (U.S. Pat. No. 3,574,628) and Rosecrants et al (U.S. Pat. No. 3,737,313) or emulsions containing weak silver halide solvents, such as ammonium salts, as illustrated by Perignon (U.S. Pat. No. 3,784,381) and Research Disclosure, September 1994, Item 36544. Moreover, a soluble silver salt can be reacted with a soluble halogen salt using the single jet method, the double jet method and combinations thereof. The method of forming grains in the presence of an excess of silver ions (the so-called 'reverse mixing method') can also be used. The 'controlled double jet method' (also called 'controlled diffusion method') is preferred. According to this method, the pAg of the liquid phase (in which the silver halide is to be produced) is kept constant or varied systematically to provide emulsions with the desired properties. This method can provide silver halide emulsions having a regular crystal form and an almost uniform grain size. The crystal form of the silver halide grains in the photographic emulsion may be regular (such as cubic or octahedral) or irregular (such as spherical or plate-like) or a composite of these forms. The grains may comprise mixed grains having various crystal forms.

The silver halide grains in the photographic emulsion used in this invention can have a relatively wide grain size distribution, but a narrow grain size distribution is preferred. In particular, the size of the silver halide grains amounting to 90% of the total, based on the weight or number of the grains, is preferably within ±40% of the average grain size (such an emulsion is usually referred to as a monodispersed emulsion). Any silver halide (including mixed halides) can be used with silver chlorobromide being preferred (containing 60-90% chloride). These "high-chloride" grains which are preferred for the lith-type emulsions have preferably cubic shape and a monodisperse size distribution. Grain edge length is preferably in the 0.1 to 0.5 micron range and most preferably in the 0.15 to 0.3 micron range.

In order to form photographic emulsions suitable to practicing the subject invention, the individual reactants can be added to the reaction vessel through surface or subsurface delivery tubes by gravity feed or by delivery apparatus for maintaining control of the pH and/or pAg of the reaction vessel contents, as illustrated by Culhane et al (U.S. Pat. No. 3,821,002), and Oliver (U.S. Pat. No. 3,031,304), all incorporated by reference. In order to obtain rapid distribution of the reactants within the reaction vessel, specially constructed mixing devices can be employed, as illustrated by Audran (U.S. Pat. No. 2,996,287), McCrossen et al (U.S. Pat. No. 3,342,605), Frame et al (U.S. Pat. No. 3,415,650), Porter et al (U.S. Pat. No. 3,785,777), Saito et al (German OLS 2,556,885) and Sato et al (German OLS 2,555,364), as illustrated by Forster et al U.S. Pat. No. 3,897,935 and Posse et al U.S. Pat. No. 3,790,386.

The grain size distribution of the silver halide emulsions can be controlled by silver halide grain separation techniques or by blending silver halide emulsions of differing grain sizes. Two or more of silver halide emulsions which are separately prepared can be mixed and then used, if desired.

The halide content of the interior and the surface layers of the silver halide grains may be different or the grains may be uniform throughout. During formation or physical ripening of the grains, cadmium salts, zinc salts, lead salts, thallium salts, iridium, cobalt, rhodium salts or complex salts thereof, iron salts or iron complex salts, and the like can be present, as can mixtures thereof. Preferred are rhodium or iridium salts or mixtures thereof. Preferred levels of rhodium salts are $10^{-3}$ to $10^{-9}$ moles/mole Ag, and more preferred levels are $10^{-4}$ to $10^{-7}$ moles/mole Ag. Preferred levels of iridium salts are $10^{-3}$ to $10^{-11}$ moles/mole Ag, and more preferred levels are $10^{-5}$ to $10^{-8}$ moles/mole Ag.

After the formation of the precipitates or after physical ripening, the soluble salts are usually removed from the emulsion. For this purpose ultrafiltration or the well-known noodle washing method may be used. Alternatively, the flocculation method, as described by R. J. Croome *J.Phot. Sci.*, 31, 30 (1983), may be used. This method employs an inorganic salt having a polyvalent anion such as sodium sulfate, an anionic surface active agent, an anionic polymer (such as polystyrene sulfonic acid) or a gelatin derivative (such as an aliphatic acylated gelatin, an aromatic acylated gelatin or an aromatic carbamoylated gelatin). The removal of the soluble salts may be omitted, if desired.

The silver halide emulsions used in the present invention do not need to be chemically sensitized, however, chemically sensitized silver halide emulsions are preferred for high speed emulsions. Processes for chemical sensitization, of silver halide emulsions which can be used include known sulfur sensitization, reduction sensitization and noble metal sensitization processes. In addition to sulfur sensitization, selenium, tellurium, rhenium or phosphorus sensitizers or combinations of these sensitizers can be used. Chemical sensitization can be performed at pAg levels of from 5 to 10, pH levels of from 5 to 8 and at temperatures from 30° to 80° C.

These processes are described in references such as P. Glafkides, Chimie et Physique Photographique, Paul Montel, Paris (1967) or Zelikmann, Making and Coating Photographic Emulsions, The Focal Press, London (1964) or H. Frieser, Die Gundlagen der Photographischen Prozesse mit Silberhalogeniden, Akademische Verlagsgesellschaft (1968). The disclosures of these references are incorporated by reference. In the noble metal sensitization processes, a gold sensitization process is a typical process where gold compounds or mainly gold complexes are used.

Complexes of noble group VIII metals other than gold, such as those of platinum, palladium, osmium or iridium, etc. can also be used. A reduction sensitization process may be used if the process does not generate fog to a degree that causes practical difficulties. A particularly preferred chemical sensitization process for the present invention is the use of a sulfur or gold sensitization process.

Examples of sulfur sensitizing agents which can be used include not only sulfur compounds present in the gelatin per se, but also various sulfur compounds for example thiosulfates, thioureas, thiazoles or rhodanines. Examples of suitable sulfur compounds are described in U.S. Pat. Nos. 1,574,994, 2,410,689, 2,278,947, 2,728,668 and 3,656,955. Typical examples of suitable reduction-sensitizing agents include stannous salts, amines, formamidine sulfinic acid and silane compounds, methyldichlorosilane, hydrazine derivatives, aminoboranes, thiourea dioxide, hydrogen, cyanoborohydrides, etc. Reduction sensitization can also be obtained at low pAg (less than 5) or high pH (greater than 8) treatment.

Specifically contemplated is the combined use of several of the aforementioned chemical ripening techniques; in particular, gold-sulfur combinations are highly preferred.

A photographic material used in this invention may contain an anti-foggant stabilizer. Examples of anti-foggants which can be advantageously used for the photographic material used in this invention are 1, 2, 4-triazole compounds substituted with a mercapto group at the 3-position, benzotriazole compounds, 2-mercaptobenzimidazole compounds (which do not contain a nitro group), arylthiosulfinates, 2-mercaptopyrimidines, 2-mercaptothiazoles, 2-mercaptobenzothiazoles, benzothiazolium compounds (such as N-aikylbenzothiazolium halides, nitrobenzindazole, nitrobenzylidene rhodanine; substituted triazaindolizines (tetraazaindenes) or N-allylbenzothiazolium halides), 2-mercapto-1,3,4-thiazoles and aromatic thiosulphides. Antifoggants which are not effective when used alone, such as 6-nitrobenzimidazole, however, can be used in combination with any of the above advantageous antifoggants.

Useful benzotriazoles can be chosen from among conventional benzotriazole antifoggants, such as those disclosed by Land (U.S. Pat. No. 2,704,721) and Rogers et al (U.S. Pat. No. 3,265,498), both incorporated by reference. The preferred benzotriazoles for use in this invention are benzotriazole (that is, unsubstituted benzotriazole), halo-substituted benzotriazoles (e.g., 5-chlorobenzotriazole, 4-bromobenzotriazole and 4-chlorobenzotriazole) and alkyl-substituted benzotriazoles wherein the alkyl moiety contains from about 1 to 12 carbon atoms (e.g., 5-methylbenzotriazole). 5-methyl benzotriazole is most preferred. The use of 5-methylbenzotriazole as an antifoggant is illustrated by Baldassari et al (U.S. Pat. No. 3,925,086), incorporated by reference.

The photographic emulsions used in this invention can be spectrally sensitized with methine or other dyes. Suitable sensitizing dyes include cyanine dyes, merocyanine dyes, complex cyanine dyes, complex merocyanine dyes, holopolar cyanine dyes, hemicyanine dyes, styryl dyes and hemioxonol dyes. Particularly useful dyes are cyanine dyes, merocyanine dyes and complex merocyanine dyes. These dyes can contain, as a basic heterocyclic nucleus, any of the nuclei which are usually employed in cyanine dyes: a pyrroline nucleus, an oxazoline nucleus, any of the nuclei which are usually employed in cyanine dyes: a pyrroline nucleus, an oxazoline nucleus, a thiazoline nucleus, a pyrrole nucleus, an oxazole nucleus, a thiazole nucleus, a selenazole nucleus, an imidazole nucleus, a tetrazole nucleus, a pyridine nucleus and the like; one of the above-described nuclei condensed with an alicyclic hydrocarbon ring; and one of the above-described nuclei condensed with an aromatic hydrocarbon ring, such as an indolenine nucleus, a benzindoleinine nucleus, an indole nucleus, a benzoxazole nucleus, a naphthoxazole nucleus, a benzothiazole nucleus, a naphthothiazole nucleus, a benzoselenazole nucleus, a benzimidazole nucleus and a quinoline nucleus. The carbon atoms of the above-described nuclei may be substituted.

The merocyanine dyes or complex merocyanine dyes can contain, as a nucleus having a ketomethylene structure, a 5- to 6-membered heterocyclic nucleus such as a pyrazolin-5-one nucleus, a thiohydantoin nucleus, a 2-thiooxazolidin-2, 4-dione nucleus, a thiazolidin-2, 4-dione nucleus, a rhodanine nucleus or a thiobarbituric acid nucleus.

Useful sensitizing dyes are those described in, e.g., German Pat. No. 929,080, U.S. Pat. Nos. 2,231,658, 2,493,748, 2,503,776, 2,519,001, 2,912,329, 3,656,959, 3,672,897, 3,694,217, 5,236,816 and 5,238,779, and British Pat. No. 1,242,588, all incorporated by reference.

These sensitizing dyes may be used individually or in combination. A combination of sensitizing dyes is often employed particularly for the purpose of supersensitization. Typical examples of such combinations are described in, e.g., U.S. Pat. Nos. 2,688,545, 2,977,229, 3,397,060, 3,522,052, 3,527,641, 3,617,293, 3,628,964, 3,666,480, 3,679,428, 3,703,377, 3,769,301, 3,814,609 and 3,827,862, and British Pat. No. 1,344,281, all incorporated by reference. Preferred sensitizing dye combinations for films to be exposed using conventional graphic camera light sources and to be handled under red safelights are mixtures of cyanine and merocyanine dyes that orthochromatically sensitize at wavelengths between 400 and 580 nm.

Other sensitizing dyes which may be used are those which exhibit maximum sensitivity at the peak emission of some lasers such as 488 nm for the argon laser, 633 nm for the HeNe laser, 650–680 nm for the Red LED laser and 760–820 for the infra-red diode laser.

The sensitizing dyes may be present in the emulsion together with dyes which themselves do not have any spectral sensitizing effects but exhibit a supersensitizing effect when used in combination, or with materials which do not substantially absorb visible light but exhibit a supersensitizing effect when used in combination. For example, aminostilbene compounds substituted with a nitrogen-containing heterocyclic ring group (e.g., those described in U.S. Pat. Nos. 2,933,390 and 3,635,721), aromatic organic acid formaldehyde condensates (e.g., those described in U.S. Pat. No. 3,743,510), azaindene compounds, and the like, can be present. The combinations described in U.S. Pat. Nos. 3,615,613, 3,615,641, 3,617,295 and 3,635,721 are particularly useful. (The disclosure of all patents mentioned in this paragraph is incorporated by reference).

A water-soluble dye may be present in any of the hydrophilic colloid layers of the photographic light-sensitive material used in this invention, for example, as a filter dye or for prevention of light scattering, or for antihalation. Examples of these dyes include oxonol dyes, hemioxonol dyes, styryl dyes, merocyanine dyes, cyanine dyes and azo dyes. Of these dyes, oxonol dyes, hemioxonol dyes and merocyanine dyes are particularly useful. Specific examples of dyes which can be used are those described in British Pat.

Nos. 584,609 and 1,177,429, and U.S. Pat. Nos. 2,274,782, 2,533,472, 2,956,879, 3,148,187, 3,177,078, 3,247,127, 3,540,887, 3,575,704, 3,653,905 and 3,718,472, all incorporated by reference.

A hardener may be present in any of the hydrophilic colloid layers in the light-sensitive material used in this invention. These hardeners include, for example, chromium salts (such as chrome alum or chromium acetate), aldehydes (such as formaldehyde, glyoxal or glutaraldehyde), N-methylol compounds (such as dimethylolurea or methyloldimethylhydantoin), dioxane derivatives (such as 2,3-dihydroxydioxane), active vinyl compounds (such as 1,3,5-triacrylolyl-hexahydro-s-triazine), mucohalic acids (such as mucochloric acid or mucophenoxychloric acid), isooxazoles, dialdehyde starch, dichlorohydroxytriazine and carbamoyl-pyridinium compounds which can be used alone or in combination.

Specific examples of hardener compounds are described, e.g., U.S. Pat. Nos. 1,870,354, 2,080,019, 2,726,162, 2,870,013, 2,983,611, 2,992,109, 3,047,394, 3,057,723, 3,103,437, 3,321,313, 3,325,287, 3,362,827, 3,539,664 and 3,543,292, British Pat. Nos. 676,628, 825,544 and 1,270,578, and German Pat. Nos. 872,153 and 1,090,427, all incorporated by reference.

Examples of preferred hardeners are dichlorohydroxytriazine or 2-(4-dimethylcarbamoyl-pyridino) ethane sulfonate.

The light-sensitive material of this invention may contain various known surface active agents for various purposes, e.g., as a coating aid, for preventing the generation of static charges, improving slip characteristics, improving emulsion dispersion, preventing adhesion, improving photographic characteristics (e.g., accelerating development, increasing contrast, sensitization), etc.

Examples of suitable surfactants are: nonionic surface active agents such as saponin (steroids), alkylene oxide derivatives (such as polyethylene glycol, polyethylene glycol/polypropylene glycol condensates, polyethylene glycol alkyl or alkylaryl ethers, polyethylene glycol esters, polyethylene glycol sorbitan esters, polyalkylene glycol alkylamines or amides or silicone/polyethylene oxide adducts), glycidol derivatives (such as alkenylsuccinic acid polyglycerides or alkylphenol polyglycerides), aliphatic esters of polyhydric alcohols, alkyl esters of sucrose, urethanes or ethers; anionic surface active agents containing an acidic group such as a carboxy group, a sulfo group, a phospho group, a sulfuric acid ester group of a phosphoric acid ester group, such as triterpenoid type saponin, alkylcarboxylates, alkylsulfonates, alkylbenzenesulfonates, alkylnaphthalenesulfonates, alkyl sulfuric acid esters alkyl phosphoric acid esters, N-acyl-N-alkyltaurines, sulfosuccinates, sulfoalkylpolyoxyethylene alkylphenyl ethers or polyoxyethylene alkylphosphates; amphoteric surface active agents such as amino acids, aminoalkylsulfonic acids, aminoalkylsulfonic acid esters, aminoalkylphosphoric acid esters, alkylbetaines, amineimides or amine oxides; and cationic surface active agents such as alkylamine salts, aliphatic or aromatic quaternary ammonium salts, (such as pyridinium or imidazolium salts) or phosphonium or sulfonium salts containing an aliphatic or heterocyclic ring.

Specific examples of these surface active agents are those described in, e.g., U.S. Pat. Nos. 2,240,472, 2,831,766, 3,158,484, 3,210,191, 3,294,540 and 3,507,660, British Pat. Nos. 1,012,495, 1,022,878, 1,179,290 and 1,198,450, U.S. Pat. Nos. 2,739,891, 2,823,123, 3,068,101, 3,415,649, 3,666,478 and 3,756,828, British Pat. No. 1,397,218, U.S. Pat. Nos. 3,133,816, 3,441,413, 3,475,174, 3,545,974, 3,726,683 and 3,843,368, Belgium Pat. No. 731,126, British Pat. Nos. 1,138,514, 1,159,825 and 1,374,780, and U.S. Pat. Nos. 2,271,623, 2,288,226, 2,944,900, 3,253,919, 3,671, 247, 3,772,021, 3,589,906 and 3,754,924, all incorporated by reference.

In addition to the components of the photographic emulsions and other hydrophilic colloid layers described above, it is appreciated that other conventional agents compatible with obtaining relatively high contrast images can be present. For example, the photographic elements can contain developing agents (described below in connection with the processing steps), development modifiers, plasticisers and lubricants, coating aids, antistatic materials, matting agents, brighteners and color materials, these conventional materials being illustrated in Research Disclosure, September 1994, Item 36544, page 501, incorporated by reference. Preferably, the photographic emulsion also contains anti-ageing agents, useful to prolong the shelf life of the emulsion. Suitable anti-ageing agents (especially for rhodium-doped emulsions) include polyhydroxyspiro-bis-indane as disclosed in U.S. Pat. No. 4,346,167 of E. Imatomi and preferably a pyrazolone (up to 2 g/kg of emulsion) as disclosed in U.S. Pat. No. 2,751,297 of G. Hood.

The photographic elements can be image-wise exposed with various forms of energy, which encompass the ultraviolet, visible (e.g., actinic) and infrared regions of the electromagnetic spectrum as well as electron beam and beta radiation, gamma ray, X-ray, alpha particle, neutron radiation and other forms of corpuscular and wavelike radiant energy in either noncoherent (random phase) forms or coherent (in-phase) forms, as produced by lasers. Exposures can be monochromatic, orthochromatic or panchromatic. Imagewise exposures at ambient, elevated or reduced temperatures and/or pressures, including high or low intensity exposures, continuous or intermittent exposures, exposure times ranging from minutes to relatively short durations in the millisecond to nanosecond range and solarizing exposures, can be employed within the useful response ranges determined by conventional sensitometric techniques, as illustrated by T. H. James, The Theory of the Photographic Process, 4th Ed., Macmillan, 1977, Chapters 4, 6, 17, 18 and 23, incorporated by reference.

The photographic light-sensitive material of this invention can be photographically processed using known methods and known processing solutions. The processing temperature usually ranges from about 18° to about 50° C., but temperatures lower than about 18° C. or higher than about 50° C. may be used. This invention is useful for the formation of an image by development in which a silver image is formed (a black-and-white photographic processing).

The developers used for black-and-white photographic processing preferably contain, as a developing agent, aminophenols (such as N-methyl-p-aminophenol), 3-pyrazolidones (such as 1-phenyl-3-pyrazolidone), dihydroxybenzene (such as hydroquinone) and other of the aforementioned developing agents. Specific examples of the useful developing agents include hydroquinone alone, hydroquinone plus N-methyl-p-aminophenol, hydroquinone plus 1-phenyl-3-pyrazolidones, and hydroquinone plus N-methyl-p-aminophenyl plus 1-phenyl-3-pyrazolidones. Also developing agents such as reductones and ascorbates usually together with an auxiliary developing agent of the 1-phenyl-3-pyrazolidone type may be used. Moreover, the developers usually contain an antioxidant, an alkali agent, a pH buffer or the like and, if desired, a dissolving aid, a color toning agent, a development accelerator, a surface active agent, an anti-foaming agent, a water softener, a hardener, a tackifier, etc. An anti-fogging agent (such as an alkali metal halide or benzotriazole) may be present in the developer.

According to this invention, even when development is carried out using a developer containing more than about 0.15 mol/l of sulfite ions, a gamma of more than 8 can be obtained. The pH of the developer is preferably between about 10.0 and about 11.5 and more preferably between about 10 and about 11. If the pH exceeds about 12.3, the developer is unstable even when a high concentration of sulfite ions is present, and it is difficult to maintain stable photographic characteristics for more than 3 days under normal use conditions.

Fixing solutions having a composition generally employed in the art can be used in the present invention. Not only thiosulfates and thiocyanates but also organic sulfur compounds known as fixing agents can be used as fixing agents in the present invention.

Preferred examples of fixing agents which can be used in the fixing solution include water-soluble thiosulfates such as sodium thiosulfate, potassium thiosulfate, ammonium thiosulfate, etc., water-soluble thiocyanates such as sodium thiocyanate, potassium thiocyanate, ammonium thiocyanate, etc., water-soluble organic diol fixing agents containing an oxygen atom or a sulfur atom such as 3-thio-1,5-pentanediol, 3,6-dithio-1,8-octanediol, 9-oxo-3,6,12,15-tetrathio-1,17-heptadecanediol, etc., water soluble sulfur-containing organic dibasic acids and water-soluble salts thereof such as 22ethylenebisthioglycollic acid and the sodium salt thereof, etc., imidazolidinethiones such as methylimidazolidinethione, etc. These agents have been described in L. F. A. Mason, Photographic Processing Chemistry, pages 187 and 188, Focal Press (1966).

EXAMPLES

The invention will now be illustrated in the following examples which are illustrative of the invention but are not intended to limit the scope of the invention.

Example 1

A gelatino-(silver chlorobromide) emulsion containing approximately 70 percent chloride and 30 percent bromide was prepared at 40° C. for 42 minutes by a standard double jet addition technique producing silver halide grains having an average size of 0.28 micron with a size distribution of 12%. A Rhodium doped shell was incorporated during growth of the cubic shaped crystals. After removal of soluble salts by a conventional method, the emulsion was chemically ripened using labile sulfur compounds in addition with gold compounds at 60° C. for 40 minutes. This emulsion contained gelatin in the amount of 54 g per mole of silver halide.

The concentrated developer solution was prepared from the following elements as described below:

| | |
|---|---|
| KOH (45% solution) | 8 ml |
| EDTA | 1.0 g |
| Diethylenetriamine-pentaacetic acid penta sodium salt | 1.5 g |
| Sodium bromide | 4.0 g |
| Boric acid | 2.5 g |
| 1-Phenyl-5-mercapto-tetrazole | 0.025 g |
| Benzotriazole | 0.250 g |
| Sodium sulfite | 55.0 g |
| Potassium carbonate | 22.0 g |

-continued

| | |
|---|---|
| Hydroquinone | 24.0 g |
| 1-Phenyl-4-hydroxymethyl-4-methyl-3-pyrazolidone | 0.75 g |
| Diethyleneglycol | 22.0 g |
| Water to 1 L | |

The above concentrate is diluted with two equal parts of water to obtain a working solution with a working pH of 10.4.

After development the material was fixed with a conventional fixing solution, washed with water and dried.

In the examples that follow, a comparison is made between several of the preferred agents as described in the present invention and structurally analogous agents. Significant parameters for comparison include:

a) $D_{min}$—background fog optical density b) Toe Speed—relative LogE value at OD (0.1+fog)×100 c) Mid Speed—relative LogE value at OD (2.5+fog)×100 d) Shoulder speed—relative LogE value at OD (3.25+fog)×100 (e.g., a speed of 70 is one stop faster than a speed of 100)

e) $D_{max}$—maximum optical density f) Gamma—(2.4×100)=(mid speed–toe speed)

g) Pepper Level—arbitrary scale from 1 (best) to 5 (worst). In practice, 1 and 2 are acceptable, 3 is marginal and 4 or 5 is not acceptable.

h) dot Quality—determined for 50% dot, arbitrary scale from 1 (best) to 5 (worst) Dot quality 1 and 2 are useable, dot quality 4 and 5 are not useable.

The emulsion was split into 250 g portions. Each portion was identically prepared for coating by addition of the surfactant (Olin 10G) and by adjusting the gelatin quantity such that the final coating had 5.6 g silver and 3.36 g gelatin/m². To the final coating solution the hydrazides to be tested were added as aqueous solutions in the amounts (moles/mole silver) indicated in the tables below. The final coating solutions were then coated onto a subbed polyester film on a laboratory-size cascade-coater together with a protecting layer of 1.5 g gelatine/m². The system was hardened with hydroxy-dichloro-1,3,5-triazine. Results are shown in Table 4.1.

The compounds of this invention were in many instances compared with known compounds of the following structures:

T1: Compound I-6 from U.S. Pat. No. 4,994,365 (EP 0,458,708) (always used with a booster amine):

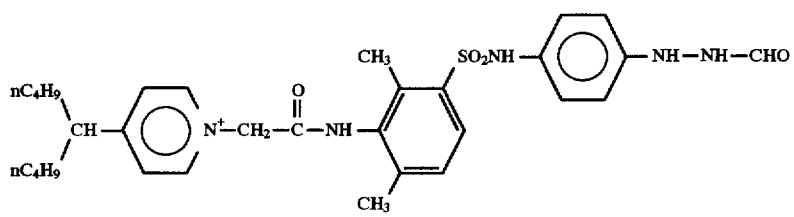

T2: Compound 1.2 from U.S. Pat. No. 4,997,980:

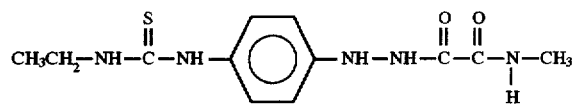

T3: Compound B-11 from U.S. Pat. No. 5,279,919:

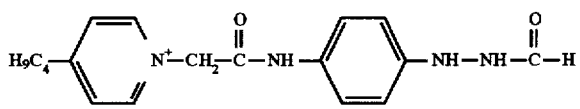

T4: Compound II-2 from U.S. Pat. No. 5,212,045:

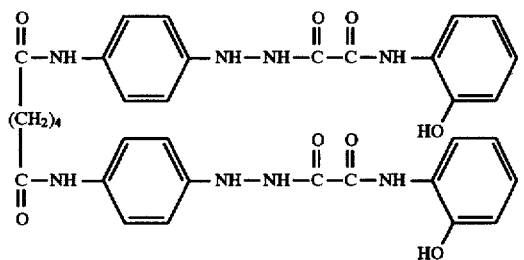

The emulsion was exposed through an optical wedge using tungsten light with 10,000 lux/sec.

The exposed material was processed in a table-top processor at 35° C. for 35 sec/developer and 35 sec fix and wash.

TABLE 4.1

Gamma Values and $D_{min}$

| Compound No. | Gamma Toe-Mid | $D_{min}$ | $D_{max}$ | Added Amount (mol/mol/Ag) |
|---|---|---|---|---|
| None | 5.29 | 0.04 | 6.13 | 0 |
| T1 | 3.24 | 0.085 | 5.96 | $0.38 \times 10^{-3}$ |
| T2 | 5.03 | 0.035 | 5.72 | $0.38 \times 10^{-3}$ |
| T3 | 6.31 | 0.03 | 5.95 | $0.38 \times 10^{-3}$ |
| T4*) | 2.67 | 0.04 | 5.91 | $0.38 \times 10^{-3}$ |
| 3.05 | 10.45 | 0.03 | 6.07 | $0.38 \times 10^{-3}$ |
| 3.06 | 10.55 | 0.03 | 6.08 | $0.38 \times 10^{-3}$ |
| 3.12 | 9.47 | 0.03 | 5.97 | $0.38 \times 10^{-3}$ |
| 3.14 | 10.10 | 0.04 | 5.67 | $0.38 \times 10^{-3}$ |
| 3.23 | 13.50 | 0.04 | 5.94 | $0.38 \times 10^{-3}$ |
| 3.24 | 11.98 | 0.03 | 5.87 | $0.38 \times 10^{-3}$ |
| 3.30 | 16.44 | 0.03 | 6.10 | $0.38 \times 10^{-3}$ |
| 3.33 | 11.20 | 0.03 | 5.92 | $0.38 \times 10^{-3}$ |
| 3.36 | 9.26 | 0.03 | 6.12 | $0.38 \times 10^{-3}$ |

*) The compound is not soluble in water and was therefore added dissolved in DMF.

The results in table 4.1 demonstrate clearly the increased gamma values and low $D_{min}$ values of the compounds of the present invention when compared to T1–T4.

Example 2

Coating solutions were prepared as in Example 1 but with the difference that they were optically sensitized with a dimethine blue spectral sensitizer. Processing was as described above. Results are given in Table 5.1

TABLE 5.1

Dot Quality

| Comp. No. | Added Amount (mol/mol Ag) | $D_{min}$ | $D_{max}$ | MID Speed | Gamma Toe-Mid | Dot Quality |
|---|---|---|---|---|---|---|
| None | 0 | 0.04 | 5.93 | 887 | 5.9 | 5 |
| T3 | $1.4 \times 10^{-3}$ | 0.04 | 5.95 | 877 | 6.3 | 4 |
| T4 | $1.4 \times 10^{-3}$ | 0.04 | 5.91 | 873 | 2.7 | 4 |
| 3.05 | $1.4 \times 10^{-3}$ | 0.05 | 5.31 | 869 | 18.4 | 1 |
| 3.06 | $1.4 \times 10^{-3}$ | 0.06 | 5.81 | 874 | 17.1 | 1 |
| 3.06 | $1.2 \times 10^{-3}$ | 0.05 | 5.54 | 873 | 15.0 | 2 |
| 3.10 | $1.4 \times 10^{-3}$ | 0.05 | 5.39 | 860 | 30.0 | 3 |
| 3.11 | $1.1 \times 10^{-3}$ | 0.04 | 5.59 | 860 | 34.2 | 2 |
| 3.11 | $1.4 \times 10^{-3}$ | 0.05 | 5.62 | 859 | 30.0 | 2 |
| 3.12 | $1.4 \times 10^{-3}$ | 0.06 | 5.42 | 871 | 30.0 | 2 |
| 3.14 | $1.4 \times 10^{-3}$ | 0.07 | 5.33 | 863 | 34.2 | 2 |
| 3.29 | $1.4 \times 10^{-3}$ | 0.05 | 5.34 | 861 | 20.0 | 1 |
| 3.29 | $1.2 \times 10^{-3}$ | 0.05 | 5.69 | 866 | 15.0 | 2 |
| 3.30 | $1.2 \times 10^{-3}$ | 0.05 | 5.10 | 858 | 15.0 | 1 |
| 3.31 | $1.4 \times 10^{-3}$ | 0.05 | 5.31 | 866 | 18.4 | 2 |
| 3.31 | $1.2 \times 10^{-3}$ | 0.05 | 5.44 | 866 | 16.0 | 2 |
| 3.33 | $1.4 \times 10^{-3}$ | 0.05 | 5.55 | 861 | 24.0 | 1 |
| 3.33 | $1.2 \times 10^{-3}$ | 0.05 | 6.00 | 861 | 21.8 | 1 |

The results in Table 5.1 show that the examples embodying the present invention had high $D_{max}$, low $D_{min}$ and extremely good dot qualities when compared to examples T3 and T4.

Example 3

TABLE 6.1

Variation of pH
The samples were prepared as in example 2 but the compounds were added dissolved in DMF.
Processing conditions were varied as indicated in Tables 6.1–6.3.

| Compound No. | pH 11 | | pH 10.75 | | pH 10.5 | | Added Amount (mol/mol Ag) |
|---|---|---|---|---|---|---|---|
| | Gamma | $D_{min}$ | Gamma | $D_{min}$ | Gamma | $D_{min}$ | |
| None | 5.34 | 0.04 | 5.53 | 0.04 | 5.40 | 0.04 | 0 |
| T2 | 0.86 | 1.31 | 3.52 | 0.83 | 3.31 | 0.68 | $0.75 \times 10^{-3}$ |
| T1 | 1.81 | 2.78 | 1.75 | 0.63 | 3.96 | 0.12 | $0.75 \times 10^{-3}$ |
| 3.12 | 13.28 | 0.04 | 9.87 | 0.04 | 6.93 | 0.04 | $0.38 \times 10^{-3}$ |
| 3.07 | 10.94 | 0.04 | 10.53 | 0.04 | 8.83 | 0.04 | $0.38 \times 10^{-3}$ |

The results in table 6.1 establish that the examples embodying the present invention have low $D_{min}$. Gradation is considerably higher within the practical pH range when compared to examples of the known state of the art. Compounds T1 and T2.

Example 4

TABLE 6.2

Variation of Processing Time
The samples were prepared as Example 2, but the compounds were added dissolved in DMF.
Processing conditions were varied as indicated in Tables 6.1–6.4.

| comp. No. | 30 sec Gamma | $D_{min}$ | 40 sec Gamma | $D_{min}$ | 50 sec Gamma | $D_{min}$ | Added Amount (mol/mol Ag) |
|---|---|---|---|---|---|---|---|
| None | 5.33 | 0.03 | 5.56 | 0.04 | 5.29 | 0.04 | 0 |
| T2 | 1.58 | 0.52 | 3.51 | 0.82 | 3.04 | 0.83 | $0.75 \times 10^{-3}$ |
| T1 | 3.20 | 0.13 | 1.79 | 0.62 | 1.79 | 0.98 | $0.75 \times 10^{-3}$ |
| 3.12 | 6.39 | 0.03 | 10.99 | 0.03 | 9.34 | 0.05 | $0.38 \times 10^{-3}$ |
| 3.07 | 8.46 | 0.03 | 10.33 | 0.03 | 11.44 | 0.03 | $0.38 \times 10^{-3}$ |

The results in Table 6.2 establish that the examples embodying the present invention show little dependence on processing time. This fact is of considerable importance in practice.

Long Term Stability

Coatings from Example 4.1 were oven conditioned for 10 days at 43° C., then exposed and processed along with control strips which had been maintained at 5° C. Gamma and $D_{min}$ were measured and are recorded in Table 6.3, below.

TABLE 6.3

| Comp. No. | 10 d 5° C. Gamma | $D_{min}$ | 10 d 43° C. Gamma | $D_{min}$ | Added Amount (mol/mol Ag) |
|---|---|---|---|---|---|
| None | 5.61 | 0.04 | 5.49 | 0.03 | 0 |
| T2 | 2.83 | 0.76 | 1.36 | 3.20 | $0.75 \times 10^{-3}$ |
| T1 | 4.52 | 1.20 | 2.11 | 0.39 | $0.75 \times 10^{-3}$ |
| 3.12 | 10.10 | 0.04 | 9.99 | 0.03 | $0.38 \times 10^{-3}$ |
| 3.07 | 9.12 | 0.03 | 11.07 | 0.03 | $0.38 \times 10^{-3}$ |

The results in Table 6.3 establish that the compounds of the present invention have an excellent long term stability which can be seen from the fact that $D_{min}$ values remain low and Gamma values remain stable even under adverse conditions.

Example 5

A silver chlorobomide emulsion, doped with sodium hexachlororhodate at $9.5 \times 10^{-8}$ moles/mole silver, was prepared at 40° C. in a high speed mixing apparatus. The emulsion was flocculated, washed to remove excess salts, diluted with a gelatin solution, heated at 60° C. for 30 minutes at pH 6 to redisperse the silver halide crystals and then sulfur and gold sensitized. The resulting cubic momodisperse emulsion had grain size of 0.263 micron and was analyzed by X-ray diffraction to be 72 mole percent chloride and 28 mole percent bromide.

Portions of the above chemically sensitized emulsion were orthosensitized using a mixture of a merocyanine and a benzimidazolocarbocyanine dye. 5-Hydroxy-7-methyl-1,3,8-triazaindolizin and 2-mercapto-phenyltetrazole were added as stabilizers. A surface coating solution consisting of gelatin, water, coating aids, hydroquinone, Dimezone S, a crystalline silica matting agent and a gelatin hardener was prepared in a separate container.

Compound 3.38 of the invention was dissolved in a small quantity of dimethyformamide and then diluted with water and added by sidefeed addition to the emulsion solution at time of coating and at the levels shown in Table 7. Comparative dihydrazide T4 was insoluble in water and was added sidefeed to the emulsion at time of coating as a dilute solution in dimethylformamide. The solutions were cascade coated from a two slot hopper to give coatings with 3.4 g silver/meter$^2$ and a surface of 1.2 g gelatin/meter$^2$.

Strips from the coatings were exposed through a photographic step wedge using a tungsten source, the strips were processed and densities read using a densitometer. As can be seen from Table 7, coatings of compound 1.38 of the invention gave good speeds, gradients and Drains when processed for 35 sec. at a temperature of 35° C. in a developer having a pH of 10.4, as described in Example 1 (developer 2). Coatings of the comparative bihydrazide compound, T4, gave good gradients but high $D_{min}$s when processed in Anitec Reprodoff™ Developer, (developer 1) a high pH (pH 12) developer which contains an organic amine for contrast enhancement, but very low gradients when processed at pH 10.4 in developer 2. Because of the high reactivity of the compound of the invention, the coatings of this compound gave unacceptable $D_{min}$s and image quality when processed in the high pH developer 1 and results were not tabulated.

In subsequent experiments, the compounds of the invention were added directly to surface coating kettles at time of preparation as a solid or as a 10–20% solution in dimethylformamide and gave coatings with equivalent sensitometric results. The high water solubilities of the hydrazides of the invention allow them to be incorporated readily into coating solutions with little or no organic solvents or use of special dispersion techniques. The high molecular weights of the compounds minimize their diffusion from the coating layers during development and give coatings with high contrast and excellent image quality. The low reactivities of the comparative dihydrazides make them unacceptable for use in coatings for processing at low pH.

TABLE 7

| Compound No. | Developer | $D_{MIN}$ | Mid-Speed | Gamma | Amount Added (mole/ mole silver) |
|---|---|---|---|---|---|
| T4 | 1 | 0.08 | 837 | 17.1 | $2.8 \times 10^{-5}$ |
| T4 | 1 | 0.10 | 836 | 17.1 | $3.8 \times 10^{-5}$ |
| T4 | 1 | 0.16 | 833 | 9.6 | $4.4 \times 10^{-5}$ |
| T4 | 2 | 0.04 | 899 | 5.3 | $2.8 \times 10^{-5}$ |
| T4 | 2 | 0.04 | 902 | 4.8 | $3.8 \times 10^{-5}$ |
| T4 | 2 | 0.04 | 903 | 5.0 | $4.4 \times 10^{-5}$ |
| 3.38 | 2 | 0.04 | 855 | 12.6 | $4.4 \times 10^{-5}$ |
| 3.38 | 2 | 0.04 | 855 | 13.3 | $4.72 \times 10^{-5}$ |
| 3.38 | 2 | 0.04 | 854 | 14.1 | $5.0 \times 10^{-5}$ |

The results in Table 7 illustrate that the compounds of the invention provide a low $D_{min}$ and substantially higher gamma when compared with a known compound, T4.

The invention has been described above by reference to preferred embodiments but, as those skilled in the art will appreciate, many additions, omissions and modifications are possible all within the scope of the claims below.

We claim:

1. A photographic silver halide material which comprises at least one silver halide emulsion layer, wherein at least one layer of said material comprises at least one hydrazide having the general formula:

$$B-(A^+)-C\ (G^-)$$

where B and C are the same or different and have formula I:

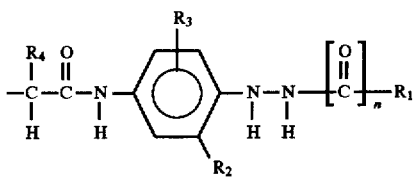

where $R_1$ is hydrogen, alkyl, alkoxy or a blocking group selected from the group consisting of

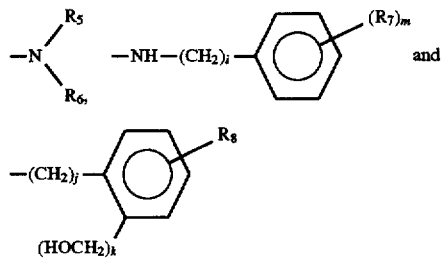

wherein $R_5$ and $R_6$ each are independently selected from the group consisting of hydrogen, alkyl, aminoalkyl, alkylaminoalkyl, acylaminoalkyl, alkylsulphonylaminoalkyl, arylsulphonylaminoalkyl, trialkylammoniumalkyl, hydroxyalkyl, haloalkyl, cycloalkyl, alkoxyalkyl, polyethyleneoxy, aryl, aralkyl, heterocyclic, and wherein $R_5$ and $R_6$ taken together can form a ring which optionally contains at least one unsaturated bond;

$R_7$ and $R_8$ are independently selected from the group consisting of hydrogen, alkyl, aralkyl, hydroxy, alkoxy, haloalkoxy, aryloxy, aralkoxy, hydroxyalkyl, acylamino, phenoxy, alkoxyalkoxy, sulphonylamino and halogen;

wherein $R_2$ and $R_3$ are independently hydrogen, alkyl, alkoxy, hydroxyalkyl, aralkyl, aralkoxy and halogen; and $R_2$ and $R_3$ taken together can form a saturated or unsaturated carbocyclic ring;

$R_4$ is hydrogen, alkyl or substituted alkyl; and m is 1 or 2; i, j and k are independently 0 or 1; and $A^+$ is an activity regulating group having the formula:

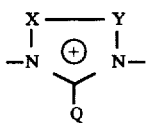

where Z denotes the elements necessary to form a 5-membered heterocyclic ring, optionally having one or two double bonds;

n is 1 or 2; and $G^-$ is a negatively charged ion.

2. The photographic material according to claim 1 wherein the activity regulating group $A^+$ has the formula II:

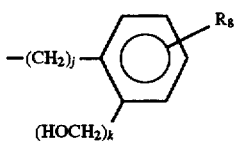

wherein Y and X denote the elements necessary to form a 5-membered heterocyclic ring having one or two double bonds; and Q is hydrogen or a ballasting group.

3. The photographic material according to claim 2 where B and C are the same and the compounds have the structure III:

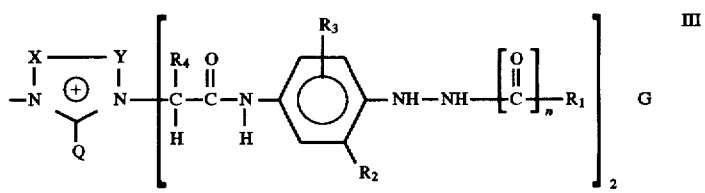

wherein $R_1$, $R_2$, $R_3$, and $R_4$ are as defined above, and Q is hydrogen or alkyl having from 1 to about 10 carbon atoms, a polyethyleneoxy group, an aryl group or a heterocyclic group, and $G^-$ is selected from the group consisting of $Cl^-$, $Br^-$, tosylate, and mesylate.

4. The photographic material according to claim 1 where the blocking group $R_1$ has the formula VI

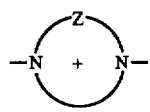

wherein $R_8$ is selected from the group consisting of hydrogen, halogen, alkoxy, alkyl, acylamino, and sulphonylamino.

5. The photographic material according to claim 1 wherein the blocking group $R_1$ has the formula VII:

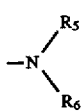

wherein $R_5$ and $R_6$ each are independently selected from the group consisting of hydrogen, alkyl, aminoalkyl, alkylaminoalkyl, acylaminoalkyl, alkylsulphonylaminoalkyl, arylsulphonylaminoalkyl, trialkylammoniumalkyl, hydroxyalkyl, haloalkyl, cycloalkyl, alkoxyalkyl, polyethyleneoxy, aryl, aralkyl, and heterocyclic;

wherein $R_5$ and $R_6$ taken together can form a substituted or unsubstituted heterocyclic ring; and n is 1 or 2.

6. The photographic material according to claim 2 wherein the activity regulating group $A^-$ is selected from the group consisting of:

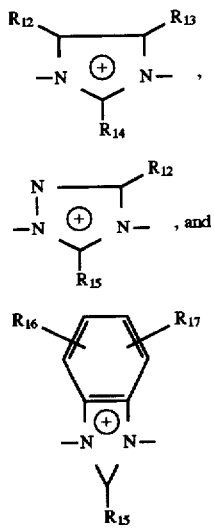

wherein $R_{12}$ and $R_{13}$ are independently selected from the group consisting of hydrogen, alkyl, alkoxy, alkoxyalkoxy, aralkyl, aryl, aralkoxy, and halogen;

$R_{14}$ and $R_{15}$ are independently selected from the group consisting of hydrogen, alkyl, alkoxy, acylamino, aralkyl, aryl, aryloxy, and a heterocyclic group; and $R_{16}$ and $R_{17}$ are independently selected from the group consisting of hydrogen, alkyl, alkoxy, alkoxylalkyl, aralkoxy, aryl, and halogen.

7. The photographic material according to claim 6 where the activity regulating group $A^+$ has the formula:

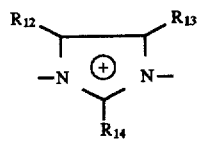

wherein $R_{12}$ and $R_{13}$ are independently selected from the group consisting of hydrogen, alkyl, alkoxy, alkoxyalkoxy, aralkyl, aryl, aralkoxy, and halogen; and $R_{14}$ is selected from the group consisting of hydrogen, alkyl, alkoxy, acylamino, aralkyl, aryl, aryloxy, and a heterocyclic group.

8. The photographic material according to claim 7, wherein $R_{12}$ and $R_{13}$ are independently selected from the group consisting of hydrogen, alkyl, and aryl; and $R_{14}$ is selected from the group consisting of hydrogen, alkyl, aryl, aralkyl, and a heterocyclic group.

9. The photographic material according to claim 8 which has the formula X:

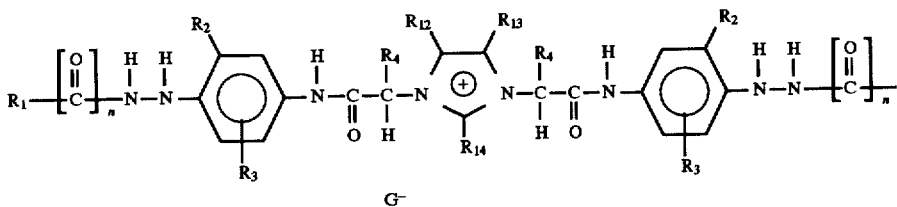

wherein $R_1, R_2, R_3, R_4, R_{12}, R_{13}, R_{14}$ and n are as defined above and $G^-$ is chloride or bromide.

10. The photographic material according to claim 3 where Q is hydrogen, an alkyl group having from 1 to 8 carbon atoms, an aryl group having from 6 to 8 carbon atoms, or a heterocyclic group having from 3 to 8 ring atoms.

11. The photographic material according to claim 10 where $R_4$ is H or methyl.

12. The photographic material according to claim 3 wherein $R_2$ and $R_3$ are independently selected from the group consisting of hydrogen, methyl, ethyl, methoxy, ethoxy, hydroxyethyl, chloro and fluoro.

13. The photographic material according to claim 12 wherein $R_2$ and $R_3$ are independently selected from the group consisting of hydrogen, methyl, and methoxy.

14. The photographic material according claim 1 where the blocking group $R_1$ has the formula V

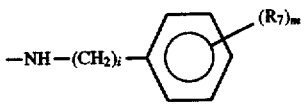

where in $R_7$ is selected from the group consisting hydrogen, hydroxy, alkyl, alkoxy, phenoxy, halogen, hydroxyalkyl, alkoxyalkoxy, and hydroxyalkoxy; and m is 1 or 2.

15. The photographic material according to claim 14 wherein each $R_7$ is independently selected from the group consisting of hydrogen, hydroxy, methyl, ethyl, methoxy, ethoxy, hydroxymethyl, hydroxyethyl, chloro, and fluoro; m is 1 and n is 2.

16. The photographic material according to claim 4 wherein $R_8$ is selected from the group consisting of hydrogen, methoxy, ethoxy, halogen, alkyl having from 1 to about 10 carbon atoms, acylamino having from 1 to about 10 carbon atoms, and sulphonylamino having from 6 to 10 carbon atoms; k is 1 and n is 1.

17. The photographic material according to claim 5 wherein $R_5$ and $R_6$ are independently selected from the group consisting of hydrogen, alkyl, hydroxyalkyl, haloalkyl, cycloalkyl, aralkyl and methoxyethyl; wherein each of the alkyl groups have from 1 to about 8 carbon atoms, each of the cycloalkyl groups have from 3 to about 10 carbon atoms and the aryl groups have from 6 to about 8 carbon atoms, or $R_5$ and $R_6$ are taken together to form a heterocyclic ring having from 3 to 6 atoms and n is 2.

18. The photographic material according to claim 8 wherein $R_{12}$ and $R_{13}$ are independently selected from the group consisting of hydrogen, methyl, ethyl, methoxy, and ethoxy; and $R_{14}$ is selected from the group consisting of hydrogen, alkyl having from 1 to about 8 carbon atoms, phenyl, tolyl, and benzyl, furyl and thienyl.

19. The photographic material according to claim 9 wherein $R_2$, $R_3$, $R_4$, $R_{12}$ and $R_{13}$ are independently hydrogen or alkyl having from 1 to about 6 carbon atoms and $R_{14}$ is alkyl having from 1 to about 8 carbon atoms.

20. The photographic material according to claim 19 wherein $R_1$ is 2-hydroxymethylphenyl and $R_2$, $R_3$, $R_4$, $R_{12}$ and $R_{13}$ are independently hydrogen or methyl.

21. The photographic material according to claim 20 wherein $R_2$, $R_3$, $R_4$, $R_{12}$ and $R_{13}$ are hydrogen, $R_{14}$ is ethyl and n is 1.

22. The photographic material according to claim 9 wherein the blocking group $R_1$ is a 2-hydroxyanilyl group and n is 2.

23. The photographic material according to claim 22 wherein the blocking group $R_1$ is 2-hydroxy-4-methylanilyl and $R^2$, $R^3$, $R^4$, $R^{12}$ and $R^{13}$ are independently hydrogen or alkyl having from 1 to about 8 carbon atoms and n is 2.

24. The photographic material according to claim 23 wherein $R_2$, $R_3$, $R_4$, $R_{12}$ and $R_{13}$ are hydrogen, $R_{14}$ is ethyl.

25. The photographic material according to claim 9 wherein the blocking group $R_1$ is a hydroxyalkylamino group and n is 2.

26. The photographic material according to claim 25 wherein the blocking group $R_1$ is 2-hydroxyethyl amino and n is 2.

27. The photographic material according to claim 26 wherein $R_2$, $R_3$, $R_4$, $R_{12}$ and $R_{13}$ are hydrogen, $R_{14}$ is ethyl.

* * * * *

UNITED STATES PATENT AND TRADEMARK OFFICE
CERTIFICATE OF CORRECTION

PATENT NO. : 5,702,866
DATED : December 30, 1997
INVENTOR(S) : Mario FRYBERG et al.

It is certified that error appears in the above-indentified patent and that said Letters Patent is hereby corrected as shown below:

Title page, [30], Foreign Application Priority Data, change "9410415" to --9410425.4--.

Signed and Sealed this

Twenty-third Day of June, 1998

Attest:

BRUCE LEHMAN

Attesting Officer  Commissioner of Patents and Trademarks